United States Patent
Dawson et al.

(10) Patent No.: US 8,329,394 B2
(45) Date of Patent: Dec. 11, 2012

(54) METHODS AND SUBSTANCES FOR ISOLATION AND DETECTION OF SMALL POLYNUCLEOTIDES

(75) Inventors: Ellott P. Dawson, Murfreesboro, TN (US); Kristie E. Womble, Franklin, TN (US)

(73) Assignee: Bioventures, Inc., Murfreesboro, TN (US)

( * ) Notice: Subject to any disclaimer, the term of this patent is extended or adjusted under 35 U.S.C. 154(b) by 452 days.

(21) Appl. No.: 11/958,180

(22) Filed: Dec. 17, 2007

(65) Prior Publication Data

US 2008/0102470 A1 May 1, 2008

Related U.S. Application Data

(63) Continuation-in-part of application No. PCT/US2007/077311, filed on Aug. 30, 2007.

(60) Provisional application No. 60/871,094, filed on Dec. 20, 2006, provisional application No. 60/866,210, filed on Nov. 16, 2006, provisional application No. 60/863,886, filed on Nov. 1, 2006, provisional application No. 60/825,888, filed on Sep. 15, 2006, provisional application No. 60/824,068, filed on Aug. 30, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................................................... 435/6

(58) Field of Classification Search ............. 435/6, 91.1, 435/91.2, 91.31; 536/23.1, 24.5, 24.3, 24.33; 935/77, 78
See application file for complete search history.

(56) References Cited

U.S. PATENT DOCUMENTS

| | | | | |
|---|---|---|---|---|
| 5,629,153 | A * | 5/1997 | Urdea ................................ | 435/6 |
| 5,652,107 | A | 7/1997 | Lizardi et al. | |
| 6,306,597 | B1 * | 10/2001 | Macevicz ........................... | 435/6 |
| 6,365,731 | B1 | 4/2002 | Brown et al. | |
| 6,391,551 | B1 * | 5/2002 | Shultz et al. ........................ | 435/6 |
| 2005/0014163 | A1 * | 1/2005 | Dong et al. ........................ | 435/6 |
| 2005/0272075 | A1 * | 12/2005 | Jacobsen et al. ................... | 435/6 |
| 2006/0074041 | A1 | 4/2006 | Johnston et al. | |
| 2007/0077582 | A1 * | 4/2007 | Slepnev ............................. | 435/6 |
| 2008/0051339 | A1 * | 2/2008 | Sullenger et al. ................ | 514/12 |

FOREIGN PATENT DOCUMENTS

| | | |
|---|---|---|
| WO | 9928505 | 6/1999 |
| WO | 2006033020 | 3/2006 |
| WO | 2007024653 | 3/2007 |

OTHER PUBLICATIONS

Notification of Transmittal of and International Search Report and Written Opinion of the International Searching Authority, PCT Serial No. PCT/US07/77311, mailed Sep. 17, 2008, 9 pages.
Berezikov, E. et al., "Many novel mammalian microRNA candidates identified by extensive cloning and RAKE analysis," Genome Research, Oct. 2006, vol. 16, No. 10, pp. 1289-1298.
Notification of Transmittal and the International Search and the Written Opinion of the International Searching Authority for PCT/US08/74899, mailed Nov. 19, 2008, 10 pages.
Notification of Transmittal of International Preliminary Report on Patentability for PCT Application No. PCT/US07/77311, mailed May 13, 2009, 6 pages.
Hartig, J.S. et al., "Sequence-Specific Detection of MicroRNAs by Signal-Amplifying Ribozymes," J.Am.Chem.Soc., (2004) vol. 126, No. 3, pp. 722-723.
Allawi, H.T. et al., "Quantitation of microRNAs using a modified Invader assay," RNA (2004), vol. 10, No. 7, pp. 1153-1161.
Raymond, C.K. et al., "Simple, quantitative primer-extension PCR assay for diret monitoring of microRNAs and short-interfering RNAs," RNA, (2005) vol. 11, No. 11, pp. 1737-1744.
Supplementary European Search Report for European Application No. 07841673.2, dated Oct. 29, 2009, 9 pages.
Jia et al., "Ultrasensitive Detection of microRNAs by Exponential Isothermal Amplification," Agnew Chem. Int. Ed. 2010, 49, 5498-5501.
Van Ness et al., "Isothermal Reactions for the Amplification of Oligonucleotides," PNAS, Apr. 15, 2003, vol. 100, No. 8, p. 4504-4509.
Walker et al., "In vitro amplification of DNA by a restriction enzyme/DNA polymerase system," Proc. Natl. Acad. Sci. USA, vol. 89, pp. 392-396, Jan. 1992, Appl. Biol. Sci.

* cited by examiner

*Primary Examiner* — Jane Zara
(74) *Attorney, Agent, or Firm* — David A. Farah; Sheldon Mak & Anderson PC

(57) ABSTRACT

A capture probe suitable for use with methods for isolating, labeling or detecting small polynucleotides. A method for isolating a small polynucleotide of interest from a sample comprising hybridizing the small polynucleotide to the capture probe and lengthening the small polynucleotide by primer extension or ligation. A method for detecting a small polynucleotide of interest following isolation by amplification of the primer extension products and/or hybridization and subsequent cleavage of dual labeled detector probes.

25 Claims, 8 Drawing Sheets

SEQUENCE LISTING

<160> NUMBER OF SEQ ID NOS: 52

<210> SEQ ID NO 1
<211> LENGTH: 22
<212> TYPE: DNA
<213> ORGANISM: Artificial
<220> FEATURE:
<223> OTHER INFORMATION: Synthetic

<400> SEQUENCE: 1
aactatacaa cctactacct ca                                              22

<210> SEQ ID NO 2
<211> LENGTH: 21
<212> TYPE: DNA
<213> ORGANISM: Artificial
<220> FEATURE:
<223> OTHER INFORMATION: Synthetic

<400> SEQUENCE: 2
actatacaac ctcctacctc a                                               21

<210> SEQ ID NO 3
<211> LENGTH: 23
<212> TYPE: DNA
<213> ORGANISM: Artificial
<220> FEATURE:
<223> OTHER INFORMATION: Synthetic

<400> SEQUENCE: 3
gctacctgca ctgtaagcac ttt                                             23

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
cgcgtaccaa aagtaataat g                                               21

<210> SEQ ID NO 5
<211> LENGTH: 23
<212> TYPE: DNA
<213> ORGANISM: Artificial
<220> FEATURE:
<223> OTHER INFORMATION: Synthetic

<400> SEQUENCE: 5
tcacatagga ataaaaagcc ata                                             23

<210> SEQ ID NO 6
<211> LENGTH: 17
<212> TYPE: DNA
<213> ORGANISM: Artificial
<220> FEATURE:
<223> OTHER INFORMATION: Synthetic

<400> SEQUENCE: 6
gattcacaac accagct                                                    17

<210> SEQ ID NO 7
<211> LENGTH: 22
<212> TYPE: DNA

<213> ORGANISM: Artificial
<220> FEATURE:
<223> OTHER INFORMATION: Synthetic

<400> SEQUENCE: 7
cgaaggcaac acggataacc ta                                              22

<210> SEQ ID NO 8
<211> LENGTH: 22
<212> TYPE: DNA
<213> ORGANISM: Artificial
<220> FEATURE:
<223> OTHER INFORMATION: Synthetic

<400> SEQUENCE: 8
aataggtcaa ccgtgtatga tt                                              22

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9
taatacgact cactataggg                                                 20

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
ccctatagtg agtcgtatta                                                 20

<210> SEQ ID NO 11
<211> LENGTH: 18
<212> TYPE: DNA
<213> ORGANISM: Artificial
<220> FEATURE:
<223> OTHER INFORMATION: Synthetic

<400> SEQUENCE: 11
atttaggtga cactatag                                                   18

<210> SEQ ID NO 12
<211> LENGTH: 74
<212> TYPE: DNA
<213> ORGANISM: Artificial
<220> FEATURE:
<223> OTHER INFORMATION: Synthetic

<400> SEQUENCE: 12
atttaggtga cactatagaa ctcgagaact atacaaccta ctacctcagc tagcccctat     60
agtgagtcgt atta                                                       74

<210> SEQ ID NO 13
<211> LENGTH: 73
<212> TYPE: DNA
<213> ORGANISM: Artificial
<220> FEATURE:
<223> OTHER INFORMATION: Synthetic

<400> SEQUENCE: 13

```
atttaggtga cactatagaa ctcgagacta tacaacctcc tacctcagct agcccctata    60
gtgagtcgta tta                                                       73
```

<210> SEQ ID NO 14
<211> LENGTH: 75
<212> TYPE: DNA
<213> ORGANISM: Artificial
<220> FEATURE:
<223> OTHER INFORMATION: Synthetic

<400> SEQUENCE: 14

```
atttaggtga cactatagaa ctcgaggcta cctgcactgt aagcactttg ctagcccta     60 tagtgagtcg tatta                                                     75
```

<210> SEQ ID NO 15
<211> LENGTH: 73
<212> TYPE: DNA
<213> ORGANISM: Artificial
<220> FEATURE:
<223> OTHER INFORMATION: Synthetic

<400> SEQUENCE: 15

```
atttaggtga cactatagaa ctcgagcgcg taccaaaagt aataatggct agcccctata    60
gtgagtcgta tta                                                       73
```

<210> SEQ ID NO 16
<211> LENGTH: 75
<212> TYPE: DNA
<213> ORGANISM: Artificial
<220> FEATURE:
<223> OTHER INFORMATION: Synthetic

<400> SEQUENCE: 16

```
atttaggtga cactatagaa ctcgagtcac ataggaataa aaagccatag ctagcccta     60 tagtgagtcg tatta                                                     75
```

<210> SEQ ID NO 17
<211> LENGTH: 69
<212> TYPE: DNA
<213> ORGANISM: Artificial
<220> FEATURE:
<223> OTHER INFORMATION: Synthetic

<400> SEQUENCE: 17

```
atttaggtga cactatagaa ctcgaggatt cacaacacca gctgctagcc cctatagtga    60
gtcgtatta                                                            69
```

<210> SEQ ID NO 18
<211> LENGTH: 74
<212> TYPE: DNA
<213> ORGANISM: Artificial
<220> FEATURE:
<223> OTHER INFORMATION: Synthetic

<400> SEQUENCE: 18

```
atttaggtga cactatagaa ctcgagcgaa ggcaacacgg ataacctagc tagcccctat    60
agtgagtcgt atta                                                      74
```

<210> SEQ ID NO 19
<211> LENGTH: 74
<212> TYPE: DNA
<213> ORGANISM: Artificial
<220> FEATURE:

<223> OTHER INFORMATION: Synthetic

<400> SEQUENCE: 19
atttaggtga cactatagaa ctcgagaata ggtcaaccgt gtatgattgc tagcccctat    60
agtgagtcgt atta    74

<210> SEQ ID NO 20
<211> LENGTH: 20
<212> TYPE: DNA
<213> ORGANISM: Artificial
<220> FEATURE:
<223> OTHER INFORMATION: Synthetic

<400> SEQUENCE: 20
taatacgact cactataggg    20

<210> SEQ ID NO 21
<211> LENGTH: 20
<212> TYPE: DNA
<213> ORGANISM: Artificial
<220> FEATURE:
<223> OTHER INFORMATION: Synthetic

<400> SEQUENCE: 21
aattaaccct cactaaaggg    20

<210> SEQ ID NO 22
<211> LENGTH: 22
<212> TYPE: DNA
<213> ORGANISM: Artificial
<220> FEATURE:
<223> OTHER INFORMATION: Synthetic

<400> SEQUENCE: 22
aatttaaggt gacactatag aa    22

<210> SEQ ID NO 23
<211> LENGTH: 19
<212> TYPE: DNA
<213> ORGANISM: Artificial
<220> FEATURE:
<223> OTHER INFORMATION: Synthetic

<400> SEQUENCE: 23
gctagttatt gctcagcgg    19

<210> SEQ ID NO 24
<211> LENGTH: 52
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: deoxyuridine

<400> SEQUENCE: 24
atcagganca gctgagcctc agcattcaca taggaataaa aagccataac ac    52

<210> SEQ ID NO 25
<211> LENGTH: 46
<212> TYPE: DNA
<213> ORGANISM: Artificial
<220> FEATURE:
<223> OTHER INFORMATION: Synthetic
<220> FEATURE:

```
<221> NAME/KEY: misc_feature
<222> LOCATION: (8)..(8)
<223> OTHER INFORMATION: deoxyuridine

<400> SEQUENCE: 25
atcagganca gctgagcctc agcatgattc acaacaccag ctacac        46

<210> SEQ ID NO 26
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: deoxyuridine

<400> SEQUENCE: 26
atcagganca gctgagcctc agcatcgaag gcaacacgga taacctaaca c    51

<210> SEQ ID NO 27
<211> LENGTH: 52
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (10)..(13)
<223> OTHER INFORMATION: phosphorothioate linkages in the backbone

<400> SEQUENCE: 27
atcaggatca gctgagcctc agcattcaca taggaataaa aagccataac ac    52

<210> SEQ ID NO 28
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (10)..(13)
<223> OTHER INFORMATION: phosphorothioate linkages in the backbone

<400> SEQUENCE: 28
atcaggatca gctgagcctc agcatgattc acaacaccag ctacac        46

<210> SEQ ID NO 29
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (10)..(13)
<223> OTHER INFORMATION: phosphorothioate linkages in the backbone

<400> SEQUENCE: 29
atcaggatca gctgagcctc agcatcgaag gcacacggat aacctaacac      50

<210> SEQ ID NO 30
<211> LENGTH: 21
<212> TYPE: DNA
<213> ORGANISM: Artificial
<220> FEATURE:
<223> OTHER INFORMATION: Synthetic
```

```
<400> SEQUENCE: 30
caggatcagc tgagagcctc a                                            21

<210> SEQ ID NO 31
<211> LENGTH: 21
<212> TYPE: DNA
<213> ORGANISM: Artificial
<220> FEATURE:
<223> OTHER INFORMATION: Synthetic

<400> SEQUENCE: 31
caggatcagc tgagagcctc a                                            21

<210> SEQ ID NO 32
<211> LENGTH: 15
<212> TYPE: DNA
<213> ORGANISM: Artificial
<220> FEATURE:
<223> OTHER INFORMATION: Synthetic

<400> SEQUENCE: 32
ggctagctac aacga                                                   15

<210> SEQ ID NO 33
<211> LENGTH: 14
<212> TYPE: DNA
<213> ORGANISM: Artificial
<220> FEATURE:
<223> OTHER INFORMATION: Synthetic

<400> SEQUENCE: 33
tccgagccgg acga                                                    14

<210> SEQ ID NO 34
<211> LENGTH: 64
<212> TYPE: DNA
<213> ORGANISM: Artificial
<220> FEATURE:
<223> OTHER INFORMATION: Synthetic

<400> SEQUENCE: 34
caggacgact cgttgtagct agcctgtacc tcagcatatt cacataggaa taaaaagcca   60
taac                                                               64

<210> SEQ ID NO 35
<211> LENGTH: 57
<212> TYPE: DNA
<213> ORGANISM: Artificial
<220> FEATURE:
<223> OTHER INFORMATION: Synthetic

<400> SEQUENCE: 35
caggacgact cgttgtagct agcctgtacc tcagcatatg attcacaaca ccagcta     57

<210> SEQ ID NO 36
<211> LENGTH: 63
<212> TYPE: DNA
<213> ORGANISM: Artificial
<220> FEATURE:
<223> OTHER INFORMATION: Synthetic

<400> SEQUENCE: 36
caggacgact cgttgtagct agcctgtacc tcagcatatc gaaggcaaca cggataacct   60
aac                                                                63
```

<210> SEQ ID NO 37
<211> LENGTH: 64
<212> TYPE: DNA
<213> ORGANISM: Artificial
<220> FEATURE:
<223> OTHER INFORMATION: Synthetic

<400> SEQUENCE: 37
acattcacct cgttgtagct agccttgacc tcagcgaatt cacataggaa taaaaagcca    60
taac                                                                64

<210> SEQ ID NO 38
<211> LENGTH: 58
<212> TYPE: DNA
<213> ORGANISM: Artificial
<220> FEATURE:
<223> OTHER INFORMATION: Synthetic

<400> SEQUENCE: 38
acattcacct cgttgtagct agccttgacc tcagcgaatg attcacaaca ccagctac     58

<210> SEQ ID NO 39
<211> LENGTH: 63
<212> TYPE: DNA
<213> ORGANISM: Artificial
<220> FEATURE:
<223> OTHER INFORMATION: Synthetic

<400> SEQUENCE: 39
acattcacct cgttgtagct agccttgacc tcagcgaatc gaaggcaaca cggataacct    60
aac                                                                 63

<210> SEQ ID NO 40
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (9)..(11)
<223> OTHER INFORMATION: RNA

<400> SEQUENCE: 40
caggacgacg ugtacctca                                                19

<210> SEQ ID NO 41
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (9)..(11)
<223> OTHER INFORMATION: RNA

<400> SEQUENCE: 41
acattcaccg utgacctca                                                19

<210> SEQ ID NO 42
<211> LENGTH: 61
<212> TYPE: DNA
<213> ORGANISM: Artificial
<220> FEATURE:
<223> OTHER INFORMATION: Synthetic

```
<400> SEQUENCE: 42
atttaggtga cactatagaa actatacaac ctactacctc accctatagt gagtcgtatt    60
a                                                                  61

<210> SEQ ID NO 43
<211> LENGTH: 60
<212> TYPE: DNA
<213> ORGANISM: Artificial
<220> FEATURE:
<223> OTHER INFORMATION: Synthetic

<400> SEQUENCE: 43
atttaggtga cactatagaa ctatacaacc tcctacctca ccctatagtg agtcgtatta    60

<210> SEQ ID NO 44
<211> LENGTH: 63
<212> TYPE: DNA
<213> ORGANISM: Artificial
<220> FEATURE:
<223> OTHER INFORMATION: Synthetic

<400> SEQUENCE: 44
atttaggtga cactatagag ctacctgcac tgtaagcact tttccctata gtgagtcgta    60
tta                                                                63

<210> SEQ ID NO 45
<211> LENGTH: 60
<212> TYPE: DNA
<213> ORGANISM: Artificial
<220> FEATURE:
<223> OTHER INFORMATION: Synthetic

<400> SEQUENCE: 45
atttaggtga cactatagac gcgtaccaaa agtaataatg ccctatagtg agtcgtatta    60

<210> SEQ ID NO 46
<211> LENGTH: 62
<212> TYPE: DNA
<213> ORGANISM: Artificial
<220> FEATURE:
<223> OTHER INFORMATION: Synthetic

<400> SEQUENCE: 46
atttaggtga cactatagat cacataggaa taaaaagcca taccctatag tgagtcgtat    60
ta                                                                 62

<210> SEQ ID NO 47
<211> LENGTH: 56
<212> TYPE: DNA
<213> ORGANISM: Artificial
<220> FEATURE:
<223> OTHER INFORMATION: Synthetic

<400> SEQUENCE: 47
atttaggtga cactatagag attcacaaca ccagctccct atagtgagtc gtatta        56

<210> SEQ ID NO 48
<211> LENGTH: 61
<212> TYPE: DNA
<213> ORGANISM: Artificial
<220> FEATURE:
<223> OTHER INFORMATION: Synthetic

<400> SEQUENCE: 48
```

-continued

```
atttaggtga cactatagac gaaggcaaca cggataacct accctatagt gagtcgtatt    60
a                                                                    61

<210> SEQ ID NO 49
<211> LENGTH: 61
<212> TYPE: DNA
<213> ORGANISM: Artificial
<220> FEATURE:
<223> OTHER INFORMATION: Synthetic

<400> SEQUENCE: 49
atttaggtga cactatagaa ataggtcaac cgtgtatgat tccctatagt gagtcgtatt    60
a                                                                    61

<210> SEQ ID NO 50
<211> LENGTH: 17
<212> TYPE: RNA
<213> ORGANISM: Artificial
<220> FEATURE:
<223> OTHER INFORMATION: Sythetic

<400> SEQUENCE: 50 agcuggcuguu gugaauc                                                  17

<210> SEQ ID NO 51
<211> LENGTH: 23
<212> TYPE: RNA
<213> ORGANISM: Artificial
<220> FEATURE:
<223> OTHER INFORMATION: Synthetic

<400> SEQUENCE: 51
uauggcuuuu uauuccuaug uga                                            23

<210> SEQ ID NO 52
<211> LENGTH: 22
<212> TYPE: RNA
<213> ORGANISM: Artificial
<220> FEATURE:
<223> OTHER INFORMATION: Synthetic

<400> SEQUENCE: 52
uagguuaucc guguugccuu cg                                             22
```

METHODS AND SUBSTANCES FOR ISOLATION AND DETECTION OF SMALL POLYNUCLEOTIDES

CROSS-REFERENCE TO RELATED APPLICATIONS

The present application is a continuation-in-part of PCT Patent Application PCT/US07/77311, titled "Method and Substances for Isolating RNAs," filed Aug. 30, 2007, which claims the benefit of U.S. Provisional Patent Application 60/824,068, titled "Method and Substances for Isolating RNAs," filed Aug. 30, 2006; and claims the benefit of U.S. Provisional Patent Application 60/825,888, titled Method and Substances for Isolating RNAs,' filed Sep. 15, 2006; and claims the benefit of U.S. Provisional Patent Application 60/863,886, titled "Method and Substances for Isolating RNAs," filed Nov. 1, 2006; and claims the benefit of U.S. Provisional Patent Application 60/866,210, titled "Method and Substances for Isolating RNAs," filed Nov. 16, 2006; and claims the benefit of U.S. Provisional Patent Application 60/871,094, titled "Method and Substances for Isolating RNAs," filed Dec. 20, 2006; the contents of which are incorporated in this disclosure by reference in their entirety.

BACKGROUND

There are a large variety of small polynucleotides, both naturally occurring and synthetic, which are of scientific or commercial interest. Exemplary small polynucleotides include microRNAs, snoRNAs, short interfering RNAs (natural or synthetic), guide RNAs, nucleolar RNAs, ribosomal RNAs, tRNAs as well as small antisense DNAs or small polynucleotide degradation products. Of particular interest are microRNAs (miRNAs), naturally occurring, single stranded polyribonucleotides (polyRNAs) of between 18 and 24 RNA residues, which are derived from a longer, naturally occurring noncoding eukaryotic precursor RNA transcript (usually having a 'hairpin' configuration), and miRNAs play a significant role in cellular developmental and differentiation pathways. Consequently, there have been considerable efforts made to understand and characterize the temporal, spatial and cellular expression levels and patterns of expression of miRNAs to ascertain their precise role in cellular development and differentiation in both normal and disease states.

miRNAs are currently studied by, first, obtaining the total RNA from a sample. Next, the total RNA is fractionated into subpopulations by gel electrophoresis or by chromatographic fractionation and size selective elution. Then, the appropriate section of the gel is cut, and the 18-24 RNAs are eluted from the gel, or the eluted fraction containing single stranded RNA's in the size range of 18-24 ribonucleotides is collected, usually the RNA fraction of less than 500-200 nucleotides in length. Next, the RNAs are isolated by precipitation and the miRNAs are characterized.

However, these methods are disadvantageous because they do not work well when the amount of sample is small, such as samples from tumor tissue or biopsy material. Further, characterization of the miRNAs isolated by present methods usually comprises a several step amplification procedure followed by detection, quantitation, cloning and sequencing. Because of the large number of steps in these processes, and the notorious inefficiencies associated with the repeated purification, isolation and identification of miRNAs, it is time consuming, relatively expensive, requires relatively large amounts of material and is not fully representative of the population of miRNAs expressed within a sample, such as within a tumor, or those miRNAs expressed in low abundance. Additionally, the methods are not specific to isolating and identifying miRNAs, and often isolate and identify siRNA, tRNA, 5S/5.8SrRNA and degraded RNA from additional cellular RNAs.

Therefore, there is the need for an improved method for isolation and identification of miRNAs, other small regulatory RNAs and short interfering RNAs (siRNAs) that is not associated with these disadvantages.

SUMMARY

According to one embodiment of the invention, there is provided a capture probe for use in isolating and detecting small polynucleotides. The capture probe is a polynucleotide that includes a spacer segment having a spacer segment sequence, the spacer segment having a 3' end and a 5'end; a template segment having a template segment sequence, the template segment having a 3' end and a 5' end; and a small polynucleotide binding segment having a small polynucleotide binding segment sequence. The 5' end of the spacer segment is connected to the 3'end of the small RNA binding segment; and the 3' end of template segment is connected to the 5' end of the small RNA binding segment.

The small polynucleotide binding segment is substantially complementary to, and capable of hybridizing to, one or more than one small polynucleotides of interest by Watson-Crick base pairing. In preferred versions of the capture probe the small polynucleotide of interest is selected from the group consisting of miRNA, snoRNA, siRNA and short interfering RNA.

In one embodiment the capture probe further comprises a solid phase binding segment of a molecular composition capable of binding to a solid phase.

In one embodiment of the capture probe the spacer segment includes a RNA polymerase termination site.

In a preferred embodiment of the capture probe the small polynucleotide binding segment is substantially complementary to, and capable of hybridizing to, a miRNA of interest.

In one embodiment of the capture probe the template segment includes one or more than one sequence comprising a polynucleotide polymerase recognition site or a sequence that is complementary to a polynucleotide polymerase recognition site.

In one embodiment of the capture probe the template segment includes one or more than one sequence that is a restriction enzyme recognition motif.

In one embodiment of the capture probe the template segment includes one or more than one sequence that is complementary to a RNA-cleaving catalytic nucleic acid or DNAzyme.

One embodiment of the present invention provides a composition comprised of two or more capture probes. The composition includes (a) a first capture probe having a first spacer segment, a first small polynucleotide binding segment and a first template segment; and (b) a second capture probe having a second spacer segment, a second small polynucleotide binding segment and a second template segment, where the second small polynucleotide binding segment has a different small polynucleotide binding segment sequence than the first small polynucleotide binding segment and the second template segment has a different template segment sequence than the first template segment.

Another embodiment of the present invention provides a method of isolating a small polynucleotide of interest. The method includes the steps of (a) providing one or more than one capture probe as set forth above; (b) providing a sample comprising a small polynucleotide of interest (c) combining the capture probe and the sample; (d) allowing the small polynucleotide of interest to hybridize with the small polynucleotide binding segment of the capture probe to form a small polynucleotide/capture probe complex; (e) combining the small polynucleotide/capture probe complex with a polynucleotide polymerase, preferably a polymerase capable of using RNA as a primer, and a set of nucleotide triphosphates; and (f) extending the hybridized small polynucleotide of interest to form an extension product, where the extension product comprises the small polynucleotide of interest connected at the 3'end to an extended segment, the extended sequence comprising a sequence complementary to the template segment of the capture probe, and where the extension product is hybridized to the capture probe to form an extension product/capture probe complex.

In preferred versions of the method the small polynucleotide of interest is selected from the group consisting of miRNAs, snoRNAs, siRNAs or short interfering RNAs. In a particularly preferred version, the small polynucleotide of interest is a miRNA In one embodiment of the method, the capture probe also contains a solid phase binding segment and the small polynucleotide/capture probe complex or the extension product/capture probe complex is captured to a solid phase by binding of capture probe to a solid support via the solid phase binding segment.

Another embodiment provides a method for detecting a small polynucleotide of interest from a sample, which includes the steps of: (a) isolating a small polynucleotide of interest as set forth above, where the capture extension probe is attached to a fluorescent bead and the extended segment contains one or more labeled nucleotide residues; and (b) detecting the fluorescent bead and the labeled extension product hybridized to the capture extension probe.

Another embodiment provides a method of detecting a small polynucleotide of interest, which includes the steps of: (a) isolating a small polynucleotide of interest as set forth above, wherein the template segment of the capture probe contains one strand of an RNA polymerase recognition sequence and the extension step forms a double stranded RNA polymerase promoter; (b) combining the extension product/capture probe complex with a RNA polymerase that recognizes the double stranded RNA polymerase promoter; and (c) transcribing the sequences downstream from the promoter to synthesize a single stranded RNA product containing a small RNA binding sequence. In a preferred embodiment of the detection method, the spacer segment of the capture probe contains an RNA polymerase stop site. In another preferred embodiment, the method further comprises repeating the transcription step one or more times.

One embodiment provides another method for detecting a small RNA of interest in a sample, which includes the steps of: (a) isolating the small polynucleotide of interest as set forth above; (b) providing a ligase and a linker segment, the linker segment comprising a polynucleotide having 3' end and a 5' end, the linker segment having a linker segment sequence, wherein the linker segment sequence is substantially complementary to, and capable of hybridizing to, the spacer segment sequence by Watson-Crick base pairing; (c) allowing the linker segment to hybridize to the spacer segment; and (d) ligating the 3' end of the linker segment to the 5' end of the small RNA of interest to form a ligated extension product substantially complementary to, and capable of hybridizing to, the capture probe sequence. A preferred version of the method further comprises amplifying the ligated extension product and the capture probe by a polymerase chain reaction.

Another embodiment provides a method of detecting a small polynucleotide of interest, which includes the steps of (a) providing a dual-labeled detector probe, having one label attached to the 5' end of detector probe molecule, another label attached to the 3' end of the detector probe, and a detector probe sequence that is substantially complementary to, and capable of hybridizing to a detector probe binding sequence within the template segment of the capture probe; (b) isolating a small polynucleotide of interest as set forth above, where (1) combining the capture probe and sample further comprises adding the dual-labeled detector probe to the combination; (2) allowing the detector probe to hybridize with the detector probe binding sequence of the capture probe or small polynucleotide/capture probe complex; (3) adding a polymerase having 5' to 3' exonuclease activity and nucleotide mix to the hybridized detector probe and small polynucleotide/capture probe complex so that the detector probe is hydrolyzed by the 5' to 3' exonuclease of the polynucleotide polymerase; and (4) detecting the change in fluorescence properties of one or more of the labels following hydrolysis of the detector probe.

One embodiment provides another method of detecting a small polynucleotide of interest, including the steps of (a) isolating a small polynucleotide of interest as set forth above, where (1) the template segment comprises one or more than one sequence that is one strand of a double stranded restriction enzyme recognition motif; and (2) the extension step converts the single stranded restriction enzyme recognition sequence contained within the template segment of the capture probe into a double stranded restriction enzyme recognition sequence. The method further comprises (b) providing a restriction enzyme that recognizes and acts upon the restriction enzyme recognition sequence of the extended segment; (c) contacting the restriction enzyme with the restriction enzyme recognition sequence; (d) nicking the extension product at or near the restriction enzyme recognition sequence of the extended segment to produce a 3'ended fragment containing the small polynucleotide of interest and a 5'ended nicked extension fragment; and (e) displacing and detecting the nicked extension fragment. In one version of the method the restriction enzyme recognition motif is recognized by a nicking endonuclease. In another version the restriction enzyme recognition motif of the template segment contains one or more than one nucleotide analogue, which renders restriction enzyme recognition motif of the template segment resistant to the endonuclease activity of the restriction enzyme. In a preferred version, the method further comprises cycles of extending the 3'-ended fragment containing the hybridized small polynucleotide of interest with a polymerase such that the restriction enzyme recognition motif is rejuvenated and the 5'-ended nicked extension fragment is displaced.

In another embodiment of the detection method (a) the template segment of the capture probe comprises a first restriction site and a second restriction site, where the first restriction site differs from the second restriction site, (b) the extension step converts the first restriction site into a double stranded restriction enzyme recognition sequence capable of being nicked on the extended segment, but not the template segment, and the second restriction site is converted into a second double stranded restriction recognition sequence; (c) the nicking step comprises contacting the extension product/capture probe complex with a nicking agent which recognizes and acts on the first restriction site, but not the second restriction site, such that the extension product is selectively nicked at or near the first restriction site of the extended segment to produce a nicked extension fragment. The detecting step then comprises: (1) providing an dual labeled detector probe, which is complementary to and capable of hybridizing to the nicked extension fragment; (2) hybridizing the probe to the nicked extension fragment to form a double stranded probe/nicked extension fragment complex; (3) contacting the double stranded probe/nicked extension fragment complex with a nicking agent capable of recognizing and nicking the detector probe sequence; and (4) detecting a change in fluorescence associated with nicking the dual labeled detector probe. In a preferred version of this method, the first restriction enzyme recognition motif is recognized by a nicking endonuclease. In another version of this method, the second restriction enzyme recognition motif of the template segment contains one or more than one nucleotide analogue, which renders the restriction enzyme recognition motif of the template segment resistant to the endonuclease activity of the restriction enzyme.

In another embodiment of the detection method (a) the template segment further comprises one or more than one DNAzyme complementary sequence that is complementary to a DNAzyme motif, a first flanking segment and a second flanking segment, the first flanking segment flanking the 5'end of the DNAzyme complementary sequence and the second flanking segment flanking the 3'end of the DNAzyme complementary sequence; and (b) the displacement of the nicked extension fragment provides a functional DNAzyme capable of hybridizing to and cleaving a suitable substrate probe at a DNAzyme cleavage site. The detecting step further comprises (1) providing suitable substrate probe comprising an RNA polynucleotide or a chimeric RNA/DNA polynucleotide, the substrate probe having one label attached to the 5' end of the substrate probe molecule and another label attached to the 3' end of the substrate probe, the substrate probe comprising a first substrate probe segment having a first substrate probe sequence, a DNAzyme cleavage site and a second substrate probe segment having a second substrate probe sequence, where first substrate probe sequence of the substrate probe is substantially identical to the first flanking segment of the template segment and the second substrate probe sequence is substantially identical to the second flanking sequence of the template segment; (2) contacting the substrate probe and the nicked extension fragment such that a loop structure containing the DNAzyme motif is formed in the nicked extension fragment by Watson-Crick base pairing between the first substrate probe sequence and complementary sequences contained within the nicked extension fragment and between the second substrate probe and complementary sequences contained within the nicked extension fragment; (3) cleaving the substrate probe at the DNAzyme cleavage site; and (4) detecting a change in fluorescence associated with cleaving the substrate probe.

One embodiment provides a kit for the isolation and detection of small RNAs, which can include (1) an equimolar mix of capture probes; (2) a nucleotide mix containing deoxyribonucleotide triphosphates or ribonucleotide triphosphates; (3) a polymerase; (4) streptavidin coated paramagnetic beads; (5) one or more than one dual labeled detector probe, the detector probe having a detector probe sequence that is substantially complementary to, and capable of hybridizing to a detector probe binding sequence within the template segment of the capture probes; (6) a ligase enzyme; (7) an oligonucleotide linker that is substantially complementary to and capable of hybridizing to the spacer segment of the capture probes; and/or (8) one or more than restriction enzyme specific for a restriction enzyme recognition sequence contained in the capture probes The invention is described in more detail by the following description.

FIGURES

These and other features, aspects and advantages of the present invention will become better understood with regard to the following description, appended claims, and accompanying figures where:

DESCRIPTION

Figure 1A:
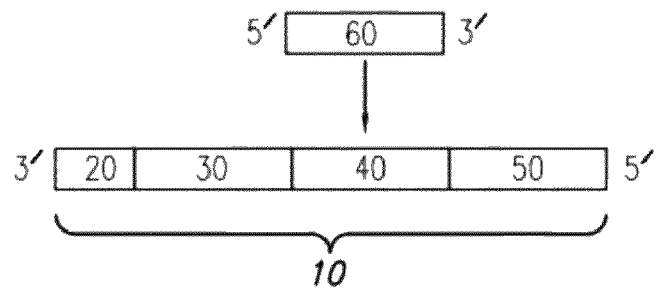
FIG. 1 is a schematic diagram of some of the steps in certain embodiments of a method of isolating and detecting miRNAs and other small polynucleotides using a capture probe according to the present invention.

According to one embodiment of the present invention, there is provided a method for isolating small polynucleotides, such as for example miRNAs (small RNAs), short interfering RNAs and other small regulatory RNAs and DNAs. According to another embodiment of the present invention, there is provided a method for identifying small polynucleotides of interest. In one embodiment, the method for identifying small polynucleotides of interest comprises, first, isolating the small polynucleotides of interest according to the present invention. According to another embodiment of the present invention, there is provided one or more than one capture probe and one or more than one set of capture probes suitable for use with a method for isolating small polynucleotides. In one embodiment, the method for isolating small polynucleotides is a method according to the present invention. The method and capture probes will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, the term "small RNAs" means a naturally occurring, single stranded RNA of between 18 and 24 RNA residues, usually with a 5' terminal phosphate group, usually referred to as "mature micro RNAs," which is derived from a larger naturally occurring precursor RNA, usually having a "hairpin" configuration.

As used in this disclosure the terms "small polynucleotide" and "small polynucleotides" refer to polynucleotides which are between 17 and 200 residues in length, usually single stranded RNA or DNA, which encompasses the group of noncoding regulatory RNAs including for example miRNAs, snoRNAs, snRNAs, siRNAs, antisense DNAs and Okazaki fragments.

As used in this disclosure, the terms "one or more than one small polynucleotides," "a small polynucleotide" and "the small polynucleotide" are intended to be synonymous, that is are intended to indicate either one small polynucleotide of interest or a plurality of small polynucleotides of interest, except where the context requires otherwise.

As used in this disclosure, the terms "one or more than one capture probe," "a capture probe," "the capture probe," "the capture probes," "capture-extension probe," "capture-extension probes," "capture and extension template probe" and "capture and extension template probes" are intended to be synonymous, and are intended to indicate either the singular or plural, except where the context requires otherwise.

As used in this disclosure, the term "substantially complementary" and variations of the term, such as "substantial complement," means that at least 90% of all of the consecutive residues in a first strand are complementary to a series of consecutive residues of the same length of a second strand. As will be understood by those with skill in the art with reference to this disclosure, one strand can be shorter than the other strand and still be substantially complementary. With respect to the invention disclosed in this disclosure, for example, the small polynucleotide or small polynucleotide binding segment can be shorter or longer than the complementary small polynucleotide of interest; however, it is preferable that the small polynucleotide binding segment is of the same length and is substantially complementary to its corresponding small polynucleotide.

As used in this disclosure, the term "hybridize" and variations of the term, such as "hybridizes" and "hybridized," means a Watson-Crick base pairing of complementary nucleic acid single strands or segments of strands to produce an anti-parallel, double-stranded nucleic acid, and as used in this disclosure, hybridization should be understood to be between substantially complementary strands unless specified otherwise, or where the context requires otherwise. As an example, hybridization can be accomplished by combining equal molar concentrations of each of the pairs of single strands, such as 100 pmoles, in the presence of 5 ug yeast tRNA in a total volume of 50 µl of aqueous buffer containing 400 mM MOPS, 80 mM DTT, and 40 mM $MgCl_2$ at a pH of 7.3, and then incubating the mixture at 25° C. for one hour while shaking gently.

As used in this disclosure, the term "near the end" and variations of the term, means within 20% of the residues of the identified end residue. For example, near the end of a 20 residue strand, means the first four residues of the identified 5' or 3' end or terminus end of the strand.

As used in this disclosure, the terms "extension" or "extension reaction" indicates the extension of the 3' end of a polynucleotide by the action of a polymerase in conjunction with all the accessory reagents and conditions for this reaction to occur.

Capture Probes

According to one embodiment of the present invention, there is provided a capture probe 10 suitable for use with a method for isolating small RNAs or DNAs. Referring to FIG. 1A, the capture probe comprises from its 3' end to its 5' end covalently joined or connected segments: a) a solid phase binding segment 20, b) a spacer segment 30, and c) a small polynucleotide binding segment 40 having a small polynucleotide binding segment sequence, where the small polynucleotide binding segment is substantially complementary to and capable of hybridizing to one or more than one small polynucleotide of interest by Watson-Crick base pairing, and d) a template segment 50.

In one embodiment, the capture probe 10 comprises a substance selected from the group consisting of one or more than one type of polynucleotide, one or more than one of polynucleotide analog, and a combination of one or more than one type of polynucleotide and polynucleotide analog.

In one embodiment the capture probe comprises a solid phase binding segment 20 of a molecular composition capable of binding to a solid phase, such as for example biotin coupled to the 3' end of the capture probe and its ability for binding to avidin or streptavidin immobilized to a solid phase, such as for example streptavidin coated paramagnetic particles or streptavidin coated wells of a microtiter plate. In another embodiment, the solid phase binding segment 20 is a substance capable of covalent binding to a solid phase, such as for example a primary amine coupled to carboxylic acid groups on a solid phase using carbodiimide activation and amide bond formation in between the primary amine of the solid phase binding segment and the carboxylic acid groups on the solid phase. Other suitable methods of covalent coupling of polynucleotides to solid phases are well known in the art. In one embodiment, the solid phase binding segment 20 is either the 3', 5' or both ends of the capture probes 10, they may also be interior to either the spacer segment 30 or the template segment 50 or both segments of the capture probes 10. Further the solid phase binding segment 20 can be added during the synthesis of the capture-extension probes 10, for example as a biotin phosphoramidite during polynucleotide synthesis as will be understood by those skilled in the art. In addition the solid phase binding segment 20 can be introduced after the synthesis of the a contiguous capture probe containing the spacer segment 30, the small polynucleotide binding segment 40 and the template segment 50, for example by the incorporation of a biotin labeled dUTP to the 3' terminus of the capture probe by the action of terminal transferase using biotinylated dUTP as the source for biotin.

Figure 2A:
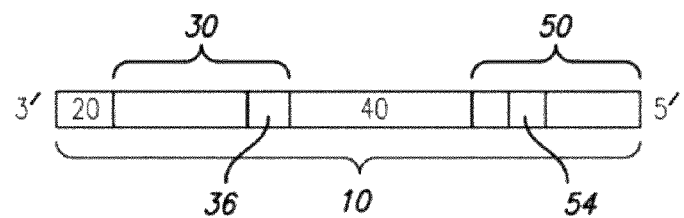
FIG. 2 is another schematic of some of the steps in certain embodiments of a method of isolating and detecting miRNAs and other small polynucleotides using one version of the capture probe having an RNA polymerase recognition site according to the present invention.

The spacer segment 30 of the capture probe comprises a polynucleotide sequence, having a predetermined sequence or predetermined size, designed to provide one or more functional features. In one embodiment, the spacer segment is of sufficient length to minimize steric hindrance of hybridization complexes forming with the polynucleotide binding segment. In one embodiment the spacer segment includes a primer binding site for amplification reactions. In another embodiment, shown in FIG. 3, the spacer segment includes a docking site for a linker in ligation reactions. In yet another embodiment, the spacer includes one or more than one desired restriction enzyme recognition site. In another embodiment, the spacer includes a RNA polymerase recognition site. In one embodiment, shown in FIG. 2A, the spacer includes a transcription termination site 36.

The polynucleotides of the spacer segment 30 may be naturally occurring, synthetic or nucleotide analogs comprising 5-50 nucleotides, or 5-40 nucleotides, preferably 5-30 nucleotides. In one embodiment, the spacer segment 30 consists of RNA. In one embodiment, the spacer segment 30 consists of DNA. In one embodiment, the spacer segment 30 consists of polynucleotide analogs. In one embodiment, the spacer segment 30 consists of a chimera of more than one polynucleotide or polynucleotide analog selected from the group consisting of RNA, DNA, polynucleotide analogs of RNA, and polynucleotide analogs of DNA. In another embodiment, the spacer segment 30 of the capture probe 10 comprises an organic substance having a carbon backbone of 6-100 carbon atoms or other backbone configurations, for example polyethelene glycols with 3-33 repeat units, or amides such as those comprised of amino caproic acid repeat units of 1-17 elements.

The small polynucleotide binding segment 40 is designed to form a hybridization complex with a polynucleotide of interest. In one embodiment, the small polynucleotide of interest is a small RNA molecule. In one embodiment, the small polynucleotide of interest is a small DNA molecule. In one embodiment, the small polynucleotide binding segment 40 consists of between 18 and 24 DNA residues. In another embodiment, the small polynucleotide binding segment 40 consists of 18 or 19 or 20 or 21 or 22 or 23 or 24 DNA residues. In another embodiment the small polynucleotide binding segment 40 comprises a DNA of between 17 and 100 polynucleotides. In another embodiment the small polynucleotide binding segment 40 comprises a DNA of between 17 and 60 polynucleotides. In another embodiment the small polynucleotide binding segment 40 comprises between 17 and 40 polynucleotides.

The small polynucleotide binding segment 40 is substantially complementary to, and capable of hybridizing to, one or more than one small polynucleotide of interest by Watson-Crick base pairing, including a small polynucleotide of interest having a predetermined sequence or having a predetermined size, from a sample comprising substances that are chemically related, such as for example, a mixture of messenger RNAs, transfer RNAs, ribosomal RNAs and genomic DNA. A small polynucleotide of interest 60 can be selected from any known small RNA from any suitable source, as will be understood by those with skill in the art with reference to this disclosure. In one embodiment, the small polynucleotide of interest 60 is selected from a public database. In a preferred embodiment, the small polynucleotide of interest 60 is an miRNA and the public database is a central repository provided by the Sanger Institute http://miRNA.sanger.ac.uk/sequences/ to which newly discovered and previously known miRNA sequences can be submitted for naming and nomenclature assignment, as well as placement of the sequences in a database for archiving and for online retrieval via the world wide web. Generally, the data collected on the sequences of miRNAs by the Sanger Institute include species, source, corresponding genomic sequences and genomic location (usually chromosomal coordinates), as well as full length transcription products and sequences for the mature fully processed miRNA.

To select the sequence or sequences of the small polynucleotide binding segment 40, when the target small RNAs comprise miRNA, a miRNA of interest or set of miRNAs of interest are selected from a suitable source, such as for example, the Sanger Institute database or other suitable database, as will be understood by those with skill in the art with reference to this disclosure. If a set of miRNAs of interest is selected from a source that contains duplicate entries for one or more than one miRNAs, in a preferred embodiment, the duplicated entries are first removed so that the set of sequences of miRNAs of interest contains only one sequence for each miRNA of interest. In one embodiment, the set of miRNAs of interest consists of one of each miRNAs from a single source or database, such as one of each miRNAs listed in the central repository provided by the Sanger Institute.

In another embodiment the small polynucleotide of interest 60 is a eucaryotic small RNA. In another embodiment the small RNA of interest is a primate small RNA. In another embodiment the small RNA of interest is a virus small RNA. In a preferred embodiment, the small RNA of interest is a human small RNA. In another embodiment, the set of small RNAs of interest are all eucaryotic miRNAs. In another embodiment, the set of small RNAs of interest are all primate miRNAs. In another embodiment, the set of small RNAs of interest are all human miRNAs.

In another embodiment the small polynucleotide of interest 60 is a eucaryotic small DNA. In another embodiment the small DNA of interest is a primate small DNA. In another embodiment the small DNA of interest is a virus small DNA. In a preferred embodiment, the small DNA of interest is a human small DNA. In another embodiment, the set of small DNAs of interest are all eucaryotic DNAs. In another embodiment, the set of small DNAs of interest are all primate DNAs. In another embodiment, the set of small DNAs of interest are all human DNAs.

Next, the small polynucleotide binding segment 40 is selected to be the substantial complement of the small polynucleotide of interest sequence 60. In a preferred embodiment, the small polynucleotide binding segment 40 is exactly the complement to the small polynucleotide of interest 60 in both length and sequence. In another embodiment, the small polynucleotide binding segment is a more than 90% complementary to a segment of the small polynucleotide of interest of the same length as the small polynucleotide of interest sequence. In another embodiment, the small polynucleotide binding segment 40 is more than 80% complementary to a segment of the small polynucleotide of interest 60 of the same length as the small polynucleotide of interest sequence 60.

In one embodiment, the small polynucleotide binding segment 40 consists of RNA. In one embodiment, the small polynucleotide binding segment 40 consists of DNA. In one embodiment, the small polynucleotide binding segment 40 consists of polynucleotide analogs. In one embodiment, the small polynucleotide binding segment 40 consists of a chimera of more than one polynucleotide or polynucleotide analog selected from the group consisting of RNA, DNA, polynucleotide analogs of RNA, and polynucleotide analogs of DNA.

Additionally, the small polynucleotide binding segment 40 can be complementary to miRNAs, snoRNAs, siRNAs or short interfering RNAs thereby facilitating their assay.

Table I provides a list of sample small polynucleotide binding segments 40 which consist of DNA along with the miRNAs that are the exact complement of the small RNA binding segments 40. As will be understood by those with skill in the art with reference to this disclosure, other small RNA binding segments 40 will also be useful, including for example small RNA binding segments 40 that are the cDNA of the small RNA binding segments 40 listed in Table I.

TABLE I

EXAMPLES OF 8 SMALL RNA BINDING SEGMENTS FOR HUMAN MIRNAS

| MICRO RNA | Small RNA binding segment as DNA polynucleotide | SEQ ID NO: |
|---|---|---|
| hsa-let-7a | AACTATACAACCTACTACCTCA | SEQ ID NO: 1 |
| hsa-let-7e | ACTATACAACCTCCTACCTCA | SEQ ID NO: 2 |
| hsa-miR-106a | GCTACCTGCACTGTAAGCACTTT | SEQ ID NO: 3 |
| hsa-miR-126* | CGCGTACCAAAAGTAATAATG | SEQ ID NO: 4 |
| hsa-miR-135a | TCACATAGGAATAAAAAGCCATA | SEQ ID NO: 5 |
| hsa-miR-138 | GATTCACAACACCAGCT | SEQ ID NO: 6 |
| hsa-miR-154 | CGAAGGCAACACGGATAACCTA | SEQ ID NO: 7 |
| hsa-miR-154* | AATAGGTCAACCGTGTATGATT | SEQ ID NO: 8 |

The template segment 50 of the capture probe comprises a polynucleotide sequence, having a predetermined sequence or predetermined size, designed to provide one or more functional features.

In a particularly preferred embodiment, the polynucleotide comprising the template segment 50 of the capture probe can serve as a template for the synthesis of a complementary polynucleotide strand by the action of a polynucleotide polymerase.

In one embodiment, shown in FIG. 4, the template segment includes a binding site for a detector probe 52.

In another embodiment, shown in FIG. 2, the template segment includes a polynucleotide polymerase recognition site 54 or that is complementary to a polynucleotide polymerase recognition site. In a preferred embodiment, the polynucleotide polymerase recognition site 54 is a motif for a polynucleotide synthesis promoter selected from the group consisting of T7, SP6, a T3 DNA dependent RNA polymerase, a type 2 RNA polymerase of *E. coli* and single stranded DNA dependent N4 RNA polymerase. The polynucleotide synthesis promoter motif can be a motif for any other suitable polynucleotide synthesis promoter, however, as will be understood by those with skill in the art with reference to this disclosure.

In one embodiment the template segment includes a transcription termination site.

In another embodiment, shown in FIG. 5, the template segment comprises one or more than one sequence that is a restriction enzyme recognition motif 56. In a particularly preferred embodiment, the specific restriction enzyme recognition motif 56, when present, is not present in the DNA analog of the miRNA or other small polynucleotide of interest that is being isolated and identified by the present methods. In a one embodiment, the restriction enzyme recognition motif 56, when present, is recognized by a nicking endonuclease. In a preferred embodiment the restriction site motif 56 of the template segment is not cut by the nicking endonuclease. In a particularly preferred embodiment, the restriction site 56 is recognized by a nicking endonuclease, such as N.BbvCI, N.AlwI, N.BstNBI, N.Bpu10I and the like available from New England Biolabs (Ipswich, Mass.). In one embodiment, the restriction enzyme recognition motif 56 is recognized by a restriction enzyme selected from the group consisting of BamHI, Hind III and EcoR I. In a preferred embodiment, the restriction site motif 56 is recognized by a restriction enzyme selected from the group consisting of Not I, Xho I, Xma I and Nhe I, because BamH I, Hind III and EcoR I also act upon some DNA equivalents of sequences of miRNA. In a preferred embodiment, the restriction enzyme recognition motif 56 contains one or more than one modified nucleotide or nucleotide analogue, which protects the template segment from the endonuclease activity of the restriction enzyme. For example, the restriction enzyme recognition motif 56 of the template segment 50 may contain one or more internucleoside bonds resistant to hydrolysis, such as phosphorothioate, boranophosphate, methylphosphonate, or peptide bonds. An alternative example of a nucleotide analogue would be where a deoxyuridine is substituted for a deoxythymidine in a restriction enzyme recognition motif 56. As will be understood by those with skill in the art with reference to this disclosure, however, other suitable restriction site motifs can also be used.

In yet another embodiment, shown in FIG. 7, the template segment 50 contains one or more than one sequence 130 complementary to a DNAzyme. Examples of a RNA-cleaving DNA enzyme (DNAzyme) include the "10-23" and the "8-17" general purpose RNA-cleaving DNA enzymes, which both contain conserved catalytic sequences (GGCTAGCTACAACGA and TCCGAGCCGGACGA, respectively). The conserved catalytic domain is flanked by variable binding domains capable of hybridizing to a target RNA by Watson-Crick base pairing. Hybridization of the flanking binding domains to a target RNA results in a loop structure containing the catalytic domain. Cleavage by an exemplary "10-23" DNAzyme occurs at a purine-pyrimidine dinucleotide of the target RNA, whereas cleavage by an exemplary "8-17" DNAzyme can occur at an AG dinucleotide of the target RNA. Accordingly, a sequence 130 complementary to a DNAzyme motif in accordance with the present embodiment will contain sequences complementary to a conserved catalytic sequence, as will be understood by one of skill in the art with reference to the present disclosure.

In one embodiment, the template segment 50 of the capture probe comprises a polynucleotide comprised of nucleotides which are naturally occurring, synthetic or nucleotide analogues.

In one embodiment, the template segment 50 comprises 1-50 nucleotides, in another embodiment the template segment comprises 1-40 nucleotides, and in yet another embodiment the template segment comprises 1-30 nucleotides.

In one embodiment, the template segment 50 consists of RNA. In one embodiment, the template segment 50 consists of DNA. In one embodiment, the template segment 50 consists of polynucleotide analogs. In one embodiment, the template segment consists of a chimera of more than one polynucleotide or polynucleotide analog selected from the group consisting of RNA, DNA, polynucleotide analogs of RNA, and polynucleotide analogs of DNA.

In a set of capture probes 10, the template segments 50 can comprise identical sequences, different sequences or different in both sequence and length. For example, template segments 50 comprising polynucleotides of different lengths in a set of capture probes 10, can be used to produce different extension products of their respective target small polynucleotides such as miRNAs. Further, extension products of different lengths can then be utilized to distinguish different target small RNAs from one another using standard methods, such as for example using capillary electrophoresis.

The synthesis of the capture probes 10 entails known methods as will be understood by those with skill in the art with reference to this disclosure. For example, the method can comprise, first, selecting the sequences of solid phase binding segment 20, the spacer segment 30, the small polynucleotide binding segment 40 and the template segment 50, and then synthesizing them. For example, in one embodiment, the 3' solid phase binding segment 20 comprises biotin, the spacer segment 30 comprises a short DNA polynucleotide segment of 5 nucleotides such as AGCTC, or a polynucleotide such as the T7 DNA dependent RNA promoter, the polynucleotide TAATACGACTCACTATAGGG (SEQ ID NO:9) or its complementary sequence CCCTATAGTGAGTCGTATTA (SEQ ID NO:10) or other polynucleotide that is not complementary to the small polynucleotide of interest 60, the small polynucleotide binding segment 40 comprises one or more complementary DNA sequence to the small RNA of interest 60, such as those listed in Table I, and the template segment 50 comprises a DNA polynucleotide sequence such as for example an SP6 DNA dependent RNA polymerase promoter 54, for example the DNA polynucleotide ATTTAGGTGACACTATAG (SEQ ID NO:11) or other polynucleotide that is not complementary to the small polynucleotide of interest.

Additionally, a restriction site 56 can be included in either or both the spacer segment 30 and the template segments 50 of the capture probes.

In a particularly preferred embodiment, the penultimate 3' end of the capture probe 10 is blocked, for example by phosphate, phosphothioate, biotin, dideoxynucleotide, 3'amine and the like, so that it cannot be extended. Such blocking of 3' ends to prevent extension is well known in the art. The purpose of such a blocking terminus is to prevent extension of the capture probe 10 by pseudo or latent terminal transferase activity inherent in several polymerases.

Synthesis of the capture probes 10 can readily be accomplished by phosphoramidite chemistry and can be obtained from a number of sources well known in the art, as will be understood by those with skill in the art with reference to this disclosure. Referring now to Table II, there are shown 8 sample capture probes 10 useful for detecting the small RNAs of interest 60 listed in the left-hand column (all of which are human miRNAs as listed in Table I).

TABLE II

| PROBE NAME | SEQUENCE | SEQ ID NO: |
|---|---|---|
| ILLUM-ED V1-7a | ATTTAGGTGACACTATAGAACTCGAGAACTATACAAC CTACTACCTCAGCTAGCCCCTATAGTGAGTCGTATTA | SEQ ID NO: 12 |
| ILLUM-ED V1-7e | ATTTAGGTGACACTATAGAACTCGAGACTATACAACCT CCTACCTCAGCTAGCCCCTATAGTGAGTCGTATTA | SEQ ID NO: 13 |
| ILLUM-ED V1-106a | ATTTAGGTGACACTATAGAACTCGAGGCTACCTGCACT GTAAGCACTTTGCTAGCCCCTATAGTGAGTCGTATTA | SEQ ID NO: 14 |
| ILLUM-ED V1-126* | ATTTAGGTGACACTATAGAACTCGAGCGCGTACCAAA AGTAATAATGGCTAGCCCCTATAGTGAGTCGTATTA | SEQ ID NO: 15 |
| ILLUM-ED V1-135a | ATTTAGGTGACACTATAGAACTCGAGTCACATAGGAA TAAAAAGCCATAGCTAGCCCCTATAGTGAGTCGTATTA | SEQ ID NO: 16 |
| ILLUM-ED V1-138 | ATTTAGGTGACACTATAGAACTCGAGGATTCACAACA CCAGCTGCTAGCCCCTATAGTGAGTCGTATTA | SEQ ID NO: 17 |
| ILLUM-ED V1-154 | ATTTAGGTGACACTATAGAACTCGAGCGAAGGCAACA CGGATAACCTAGCTAGCCCCTATAGTGAGTCGTATTA | SEQ ID NO: 18 |
| ILLUM-ED V1-154* | ATTTAGGTGACACTATAGAACTCGAGAATAGGTCAAC CGTGTATGATTGCTAGCCCCTATAGTGAGTCGTATTA | SEQ ID NO: 18 |
| PROBE ELEMENTS 5'-3' orientation | 5' SP6 SENSE, XhoI, uRNA REVCOMPL, NheI, T7 REVCOMPL, 3'Biotin optional at synthesis | |

Methods of Use

Isolation/Capture

According to another embodiment of the present invention, there is provided a method for isolating an miRNA (microRNA) or other small polynucleotides of interest from a sample comprising the small polynucleotide of interest. According to another embodiment of the present invention, there is provided a method for identifying miRNAs or other small polynucleotides. In one embodiment, the method for identifying miRNAs or other small polynucleotides comprises, first, isolating the small polynucleotides according to the present invention. Referring now to FIG. 1, there are shown some of the steps in certain embodiments of the methods. The steps shown are not intended to be limiting nor are they intended to indicate that each step depicted is essential to the method, but instead are exemplary steps only.

As can be seen in FIG. 1A, the method comprises, first, providing a sample comprising a miRNA or other small polynucleotide of interest 60. Samples suitable for analysis by the present method either comprise or potentially comprise small RNAs and small DNAs. In one embodiment, the sample further comprises one or more than one substance that is chemically related to the miRNA of interest, such as for example, a substance selected from the group consisting of messenger RNA, transfer RNA, ribosomal RNA, siRNA, 5S/5.8SrRNA, genomic DNA and a combination of the preceding. In one embodiment, the sample further comprises one or more than one RNA other than miRNA, such as for example, a substance selected from the group consisting of messenger RNA, transfer RNA, ribosomal RNA, siRNA, 5S/5.8SrRNA and a combination of the preceding. All of the RNA in the sample, regardless of the type of RNA, constitutes the "total RNA" in the sample.

In one embodiment, suitable samples are obtained from eukaryotic cells obtained from whole blood, tissue culture, cell cultures, whole tissues such as liver, lung, brain, or even whole organisms such as *C. elegans* or *Drosophila*. Small polynucleotides can also be isolated from tissues infected by some viruses as these microbes produce miRNAs which can suppress the immune response or modify other host factors to enable their persistence and infection by compromising host factors or otherwise divert host resources to their advantage. Also, small polynucleotides can occur in bacteria or procaryotes which regulate their processes such as biofilm formation and other activities of the bacteria such as pathogenicity. Such specimen sources are well known in the art.

In one embodiment, the sample is from a eukaryote. In another embodiment, the sample is from a primate. In a preferred embodiment, the sample is from a human.

In one embodiment, the sample comprises a tissue or fluid selected from the group consisting of blood, brain, heart, intestine, liver, lung, pancreas, muscle, a leaf, a flower, a plant root and a plant stem.

Cell lysates are suitable for use with the capture probes 10, especially when care has been taken to neutralize nucleases which can degrade the miRNAs or small polynucleotides to be examined in the sample or degrade the capture probes 10 contacted with the sample, however, the capture probes can be rendered resistant to the action of nucleases by their synthesis with nuclease resistant backbones such as amides such as peptide nucleic acids or more commonly phosphothioate modified backbones during their synthesis. In another embodiment the sample is a mounted, fixed tissue section, where the fixed small polynucleotides, for example miRNAs, in the sample serve as the solid phase binding segment or element 20 of the capture-extension probes 10.

In one embodiment, the method further comprises isolating the total RNA from the sample after providing the sample. In a preferred embodiment, total RNA is isolated from such specimens using methods well known in the art or using commercial kits widely available from vendors such as QIAgen, Invitrogen, Promega and the like. As will be understood by those with skill in the art with reference to this disclosure, when the method comprises isolating the total RNA from the sample after providing the sample, the term "sample" means the isolated total RNA for the remaining steps in the method.

The small polynucleotide of interest 60 has a small polynucleotide of interest sequence, and comprises 3' end and a 5' end. In one embodiment, the small polynucleotide of interest is a miRNA, which consists of between 18 and 24 RNA residues. In another embodiment, the miRNA of interest consists of 18 or 19 or 20 or 21 or 22 or 23 or 24 RNA residues.

The small polynucleotide of interest 60 is substantially complementary to, and capable of hybridizing to, a small polynucleotide binding segment 40 of a capture probe 10 according to the present invention by Watson-Crick base pairing. In one embodiment, the small polynucleotide is a miRNA of interest listed in a public database. In a preferred embodiment, the public database is a central repository provided by the Sanger Institute http:/microrna.sanger.ac.uk/sequences/ to which miRNA sequences are submitted for naming and nomenclature assignment, as well as placement of the sequences in a database for archiving and for online retrieval via the world wide web. Generally, the data collected on the sequences of miRNAs by the Sanger Institute include species, source, corresponding genomic sequences and genomic location (chromosomal coordinates), as well as full length transcription products and sequences for the mature fully processed miRNA (miRNA with a 5' terminal phosphate group).

In one embodiment, the sample provided comprises a plurality of miRNAs of interest 60, where each of the plurality of miRNAs or other small polynucleotides of interest 60 has small polynucleotide of interest sequences that are identical to one another. In one embodiment, the sample provided comprises a plurality of miRNAs of interest 60, where at least two of the plurality of miRNAs of interest 60 have miRNA of interest sequences that are different from one another. In one embodiment, the sample provided comprises a plurality of miRNAs of interest 60 comprising a first miRNA of interest having a first miRNA of interest sequence, and a second miRNA of interest having a second miRNA of interest sequence, where the first miRNA of interest sequence is different from the second miRNA of interest sequence. In another embodiment, the sample provided comprises a plurality of miRNAs of interest 60 comprising a first miRNA of interest having a first miRNA of interest sequence, a second miRNA of interest having a second miRNA of interest sequence, and a third miRNA of interest having a third miRNA of interest sequence, where the first miRNA of interest sequence is different from the second miRNA of interest sequence, where the first miRNA of interest sequence is different from the third miRNA of interest sequence, and where second miRNA of interest sequence is different from the third miRNA of interest sequence.

Next, the method further comprises providing a capture probe 10. In one embodiment, the capture probe 10 provided is a capture probe 10 according to the present invention. When the capture probe 10 is a capture probe according to the present invention, in all respects, the capture probe 10 provided has the characteristics and attributes as disclosed for a capture probe 10 according to the present invention, some of which will be repeated hereafter for clarity. As can be seen in FIG. 1, the capture probe 10 comprises three segments depicted in FIG. 1 from left to right, from the 3' end of the capture probe 10 to the 5' end of the capture probe: a) a spacer segment 30 having a spacer segment sequence; b) a small polynucleotide binding segment 40 having a polynucleotide binding segment sequence; and c) a template segment 50 having a template segment sequence, and comprising a 3' end and a 5' end, where the 5' end of the spacer segment 50 is connected to the 3' end of the polynucleotide binding segment 40, and where the 5' end of the polynucleotide binding segment 40 is connected to the 3' end of the template segment 50. The specificity of the polynucleotide binding segment 40 to an miRNA or other small polynucleotide of interest 60 allows the method to be used directly on a sample containing substances related to miRNA or on isolated total RNA without requiring the specific separation of miRNAs from the sample or from the total RNA, such as for example by either gel purification or chromatographic purification, as necessary in prior art methods.

In a particularly preferred embodiment, the penultimate 3' end of the capture probe 10 is blocked, for example by phosphate, phosphothioate, biotin, dideoxynucleotide, 3'amine and the like, so that it cannot be extended. Such blocking of 3' ends to prevent extension is well known in the art. The purpose of such a blocking terminus is to prevent extension of the capture probe 10 by pseudo or latent terminal transferase activity inherent in several polymerases.

In one embodiment, a plurality of capture probes 10 are provided as a composition or mixture comprising two or more capture probes. The mixture includes (a) a first capture probe 10 having a first spacer segment 30, a first small polynucleotide binding segment 40 and a first template segment 50; and (b) a second capture probe 10 having a second spacer segment 20, a second small polynucleotide binding segment 40 and a second template segment 50, where the second small polynucleotide binding segment 40 has a different small polynucleotide binding segment sequence than the first small polynucleotide binding segment 40 and the second template segment 50 has a different template segment sequence than the first template segment 50. The presence of different small polynucleotides bound to the capture probes 10 can thus be correlated to a detectable difference in the associated template segments 50. In a preferred embodiment, the first template segment 50 and the second template segment 50 differ in length.

Referring now to FIG. 1A, the method then comprises combining the capture probe 10 and the sample, represented in FIG. 1A by the small polynucleotide of interest 60. In a preferred embodiment, the method comprises combining the sample and the capture probe 10 in a solution.

In one embodiment, combining the capture probe 10 and the sample comprises combining approximately equimolar amounts of each capture probe 10. In another embodiment, combining the capture probe 10 and the sample comprises combining approximately equimolar amounts of each capture probe 10 with an amount of sample expected to contain approximately one tenth the molar amount of the small polynucleotide of interest 60 as of the capture probe 10. In another embodiment, combining the capture probe 10 and the sample comprises combining approximately equimolar amounts of each capture probe 10 with an amount of sample expected to contain approximately one half and one tenths and the molar amount of the small polynucleotide of interest as of the capture probe 10. In one embodiment, combining the capture probe 10 and the sample comprises combining the sample with between 0.1 pmoles and 100 pmoles/µl each of the capture probe 10 in a suitable buffer to create a solution comprising the capture probe 10 and the sample. In a preferred embodiment the amount of total RNA in the sample ranges from about 10 pg to about 10 µg, more preferably about 10 ng to about 1 µg. In a preferred embodiment, the buffer is selected from the group consisting of TRIS, MOPS, and SSC; includes alkali salts such as sodium chloride, lithium chloride or sodium citrate; and may further include nuclease inhibitors and accelerants such as dextran sulfate, polyethylene glycols or polyacrylamides. Exemplary buffers include, (a) 1×TE buffer in 0.1-2.0 M sodium chloride; (b) 0.1M MOPS in 1 mM EDTA and 100 mM sodium chloride, and (c) 20 mM MOPS, 1.8M Lithium Chloride, 1 mM EDTA, 100 µM aurintricarboxylic acid pH 6.8. As will be understood by those with skill in the art with reference to this disclosure, the pH selected for the buffer will be one that optimizes the intended reactions. In general, the pH selected will be between 6 and 8, preferably between 6.4 and 7.4 and more preferably, near 7.0. In a preferred embodiment, the method further comprises adding one or more than one RNAse inhibitor to the combination of the sample and the capture probe 10 such as for example an RNAase or nuclease inhibitor selected from the group consisting of lithium dodecylsulfate (LiDS), sodium dodecylsulfate, the ammonium salt of aurintricarboxylic acid and sodium salt of aurintricarboxylic acid, beta mercaptoethanol, dithiothreitol, Tris(2-Carboxyethyl)-Phosphine Hydrochloride (TCEP) or human placental RNAse inhibitor. Such inhibitors are included to inhibit nucleases without compromising the ability of the probes and their target polynucleotides to hybridize with one another as will be understood by those skilled in the art.

Figure 1B:
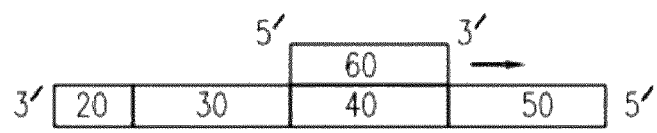

Referring now to FIG. 1B, after combining the capture probe 10 and the sample, the method comprises allowing the small polynucleotide of interest 60 to hybridize with the small polynucleotide binding segment 40 to form a small polynucleotide/capture probe complex (FIG. 1B). In one embodiment, allowing the small polynucleotide of interest 60 to hybridize with the small polynucleotide binding segment 40 comprises incubating the solution comprising the capture probe 10 and the sample for between 1 minute and 60 minutes at between 25° C. and 60° C. until substantially all of the miRNA of interest 60 has hybridized to the capture probes 10, thereby sequestering the small polynucleotide of interest 10 from other substances in the sample.

In addition to the small polynucleotide binding segment 40, the capture probes 10 also contain a solid phase binding segment 20, a spacer segment 30 and a template segment 50 capable of serving as a template for a polynucleotide polymerase. The set of capture probes 10 and hybridized target RNAs 60 are then captured to a solid phase, for example by binding of biotinylated capture probes 10 to streptavidin coated paramagnetic particles followed by temporary immobilization of the paramagnetic particles by the action of a magnet and removal of the remaining biological sample. Unlike other methods for determining small polynucleotides such as miRNAs, using the method of this disclosure permits the recovery and further processing of the removed biogical sample to be analyzed for other molecular species such as mRNAs or genomic DNA This is followed by cycles of washing the particles after their release into a wash buffer to remove unhybridized polynucleotides and other materials from the paramagnetic beads and the capture-extension probe hybridization complexes.

One advantage for the immobilized capture probe 10 methods is that initial enrichment of the total RNA sample for non-protein-coding RNAs, such as small nucleolar RNAs, siRNAs, microRNAs and antisense RNAs, is not necessary.

Preferably, the capture probe 10 will hybridize to the specific target in solution. Secondly, when the capture probe 10 is immobilized on the solid support, unbound material can be removed and thereby enrichment for the specific target has been performed. Another advantage is that buffer exchange can be facilitated. Yet another advantage is that at this point the small polynucleotides can be eluted from the bound capture probes. The eluted small polynucleotides are highly concentrated and enriched and are suitable for use in a wide variety of downstream analytical methods, such elution methods being well understood in the art for example use of water or formamide at 80° C., such downstream applications as gel electrophoresis, ligation and sequencing, labeling and hybridization and the like.

Extension

Figure 1C:
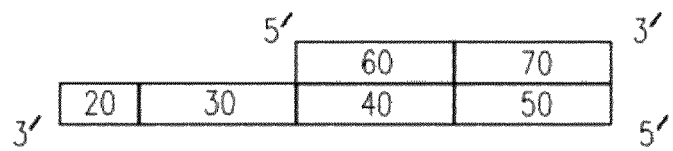
Figure 1D:
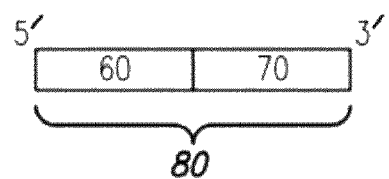

Next, as shown in FIG. 1B, the method comprises an extension reaction. The first step of the extension reaction comprises combining the small polynucleotide/capture probe complex with a polynucleotide polymerase and a set of nucleotide triphosphates. The extension reaction further comprises extending the hybridized small polynucleotide of interest 60 to form an extension product 80, where the extension product 80 is hybridized to the capture probe 10 to form an extension product/capture probe complex (FIG. 1C). The extension product is comprised of the small polynucleotide of interest 60 connected at the 3'end to an extended segment comprising a sequence complementary to the template segment 50 of the capture probe 10 (FIG. 1D). In one embodiment of the invention, the extended segment contains one or more labeled or modified nucleotide residues.

Typically, the nucleotide polymerization comprises a DNA polymerization to obtain a RNA-DNA chimera, which constitutes the extension product 80. In one embodiment of the invention, the hybridized small polynucleotides 60 bound to the capture probes 10 are extended by the action of polymerase that can utilize the hybridized small RNA as a primer. In another embodiment, where the extension template segment 50 of the capture-extension probe 10 is DNA, the polymerase is a DNA dependent DNA polymerase capable of using the 3'end of the hybridized small polynucleotide 60 as a primer. In another embodiment, the polymerase is a polynucleotide polymerase that can use RNA as primer such as T4, T7, *E. coli* Pol I, MMLV reverse transcriptase, Bst polymerase, Phi-29 polymerase and the like or a combination of one or more of these enzymes. In a preferred embodiment, the polynucleotide polymerase lacks any nuclease activity and can readily utilize labeled nucleotide triphosphates as substrates for its extension of the hybridized small polynucleotide, such as miRNA which serves as a primer for the extension reaction.

The nucleotide mixture for the extension reaction is usually a set of nucleotide triphosphates, usually NTPs, e.g. ATP, CTP, GTP and UTP, or dNTPs, e.g., dATP, dCTP, dGTP and TTP (or dUTP). In one embodiment at least one of the nucleotide triphosphates contains a detectable label such as fluorescein, cyanine 3, cyanine 5 biotin, aminoallyl, Digoxigenin, Tetramethyl Rhodamine and the like. A wide variety of detectable nucleotide triphosphates are available commercially from Roche (Indianapolis, Ind.), Invitrogen (Carlsbad, Calif.) and others. In a preferred embodiment, the labeled nucleotide triphosphate is at a lower concentration than the other three nucleotide triphosphates. For example, in one embodiment, the unlabelled nucleotide triphosphates are at a concentration in the extension reaction at between 50 and 300 micromolar and the labeled nucleotide triphosphates are at a concentration of between 5 and 30 micromolar. However, as will be understood in the art, different polymerases have different capacities to utilize such modified nucleotides in strand synthesis. Accordingly, in some cases the labeled nucleotide triphosphate may be utilized at concentrations comparable to the non-labeled nucleotide triphosphates employed in the extension reaction. Such adjustments in nucleotide triphosphate concentrations are well known in the art. Additionally, it is known in the art that the buffers and or temperatures utilized in the extension reaction can be adjusted to accommodate the incorporation of modified nucleotide triphosphates in the extension reaction.

The buffer selected for the extension reaction should not interfere with the hybridization of the small polynucleotide 60 with its capture probe 10 and be compatible with the extension reaction caused by the polymerase. Preferred versions of the buffer permit or facilitate the incorporation of modified nucleotides into the extension product.

In one embodiment the polymerase is a nuclease free form of the Klenow enzyme from *E. coli*, the nucleotide triphosphates are dATP, dCTP, dGTP at 100 micromolar each, the labeled dNTP is dUTP labeled with cyanine 3 at a concentration of 10 micromolar, and the extension buffer comprises 0.05M Tris-HCL, 0.01M $MgCl_2$, 1.0 mM DTT, 0.05 mg/ml BSA and 20 units of an RNase inhibitor such as a recombinant mammalian protein capable of inhibiting eukaryotic RNases.

Detection/Identification

Analysis of extension products 80 can be performed using techniques known in the art including, without limitation, hybridization and detection by the use of a microarray specific for the miRNAs or other small polynucleotides to be evaluated, polymerase chain reaction (PCR)-based analysis, sequence analysis, flow cytometry and electrophoretic analysis.

It will also be understood by those skilled in the art that the set of capture probes 10 could be initially bound to a solid phase such as fluorescently coded beads with coded beads assigned to identify each capture-probe according to its specificity or complementarity to a given small polynucleotide. In one embodiment each uniquely coded bead in the set of coded beads corresponds to a unique miRNA within the set of miRNAs to be evaluated. Such coded beads for assay by flow methods are available from a number of vendors such as Luminex, (Austin, Tex.). It will be understood by those skilled in the art that the set of coded beads is then contacted with the biological sample containing the miRNAs to be evaluated or measured under suitable conditions for hybridization. Further, the hybridized beads are then subjected to washing to remove nonhybridized materials and other components present in the sample. The beads are then extended in the presence of labeled dNTP(s) by the action of a DNA polymerase as set forth above. It is possible to then directly assay the plurality of coded beads for the presence and quantity of miRNAs or other small polynucleotides in the biological sample. To reduce background and noise it may be desirable to remove the unbound components of the extension reaction from the beads by washing them and then performing the analysis by flow detection, such methods being well understood in the art.

Reverse Transcription

Subsequent amplification, detection, and/or identification of the polynucleotide of interest 60 in many embodiments may further comprise reverse transcription of the resulting extension product 80 to produce cDNA. The design of suitable reverse transcription primers and use of reverse transcriptase to produce cDNA copies of extension products may can be accomplished by any means known to one of skill in the art with reference to the present disclosure.

Amplification

The terms "PCR reaction", "PCR amplification", "PCR", "pre-PCR" and "real-time quantitative PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification (NASBA™, Cangene, Mississauga, Ontario) and Q Beta Replicase systems. The products formed by said amplification reaction may or may not be monitored in real time or only after the reaction as an end point measurement.

RNA Amplification

In one embodiment, shown in FIG. 2, the method further comprises converting a partial RNA polymerase recognition sequence 54 contained within the template segment 50 or spacer segment 30 of the capture probe into a complete RNA polymerase recognition sequence 54 and 72 and ultimately into a double stranded RNA polymerase promoter 54 and 72. Subsequent RNA transcription using an RNA polymerase that recognizes the double stranded RNA polymerase promoter 54 and 72 results in the production of amplified single stranded RNA molecules. Such single stranded RNA molecules 90 find utility in various downstream applications, including gene expression studies involving nucleic acid microarrays and knockout of corresponding miRNA or other RNA complementary to the transcript by antisense or RNAi activity within cells.

The term "RNA polymerase recognition sequence" is intended to cover both single stranded and double stranded nucleotide sequences 54 and 72. When in single stranded form, the nucleotide sequence corresponds to the template or non-template strand of a double-stranded RNA polymerase promoter. "Template strand" refers to a strand of nucleic acid on which a complementary copy is synthesized from nucleotides or nucleotide analogs through the activity of a template-dependent nucleic acid polymerase. "Non-template strand" refers to the nucleic acid strand that is complementary to the template strand. When in double stranded form, the nucleotide sequences correspond to both the template and non-template strands of a double-stranded RNA polymerase promoter.

In one embodiment the template segment of the capture probe contains the non-template strand of a RNA polymerase recognition site 70. In another embodiment the spacer segment contains the template strand of a RNA polymerase recognition site.

Any RNA polymerase recognition sequence 54 can be used in the methods described herein, so long as it is specifically recognized by an RNA polymerase. Preferably, the RNA polymerase recognition sequence used is recognized by a bacteriophage RNA polymerase, such as T7, T3, or SP6 RNA polymerase. An exemplary T7 RNA polymerase recognition sequence is TAATACGACTCACTATAGGG (SEQ ID NO: 20). An exemplary T3 RNA polymerase recognition sequence is AATTAACCCTCACTAAAGGG (SEQ ID NO: 21). An exemplary SP6 RNA polymerase recognition sequence is AATTTAAGGTGACACTATAGAA (SEQ ID NO: 22).

Figure 2B:
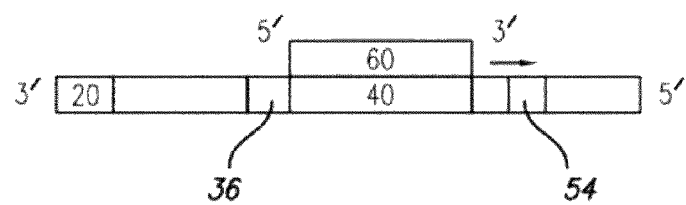

For example, with reference to FIG. 2B, a small polynucleotide of interest 60 (e.g., mRNA, hnRNA, rRNA, tRNA, miRNA, siRNA, snoRNA, non-coding RNAs, antisense DNAs, etc.) hybridizes to the small polynucleotide binding segment 40 of a capture probe 10, wherein the template segment 50 contains the required RNA polymerase recognition site 54 (in the case of FIG. 2B, the non-template strand of the RNA polymerase promoter).

Figure 2C:
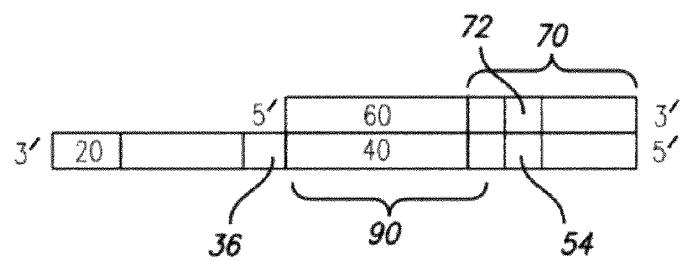

The subsequent extension product 80 comprises the polynucleotide of interest 60 and an extended segment 70 adjacent to the 3' end of the small polynucleotide of interest containing a sequence complementary to the to the RNA polymerase recognition site of the template segment 50 (FIG. 2C). The double stranded region comprising the RNA polymerase recognition site 54 and its complementary sequence 72 generates an RNA polymerase promoter.

Figure 2D:
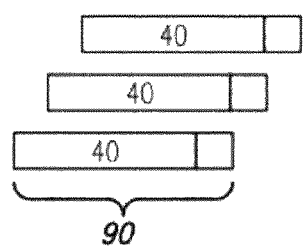

In one embodiment, in order to detect a polynucleotide of interest 60, the extension product 80 formed as described above is transcribed using an RNA polymerase which recognizes the RNA polymerase promoter 54 and 72 located at the opposite end of the extension product 80, such that an RNA product 90 is formed comprising a sequence 40 complementary to the polynucleotide of interest. Combining the double stranded extension product/capture probe complex with an RNA polymerase, which recognizes the RNA polymerase promoter 54 and 72, produces a single stranded RNA product containing sequences complementary to the small polynucleotide of interest, i.e., a cRNA 40 (FIG. 2D). In one aspect 90, the spacer segment 30 of the capture probe 10 can include an RNA polymerase stop site 36, for example the T7 stop sequence GCTAGTTATTGCTCAGCGG (SEQ ID NO:23). In this case the cRNA transcripts 90 will contain residues immediately adjacent to and downstream from the RNA polymerase recognition site 54 terminating at the 3' end at the residue preceding the stop site 36. If the stop site 36 is omitted then the enzyme will polymerize the entire sequence downstream of the start of transcription in the promoter motif, including 40 the complement of the polynucleotide of interest and any other sequence appended to the 5' end of the polynucleotide of interest 60, e.g., by ligation of an linker segment.

Preferably the transcription reaction occurs in the presence of ribonucleotides, including labeled ribonucleotides. In one aspect, the nucleotides are labeled. If it is desired to prepare a labeled polynucleotide comprising cRNA, unlabeled UTP can be omitted and replaced with or mixed with labeled UTP. Labels can include, for example, fluorescent labels or radiolabels.

Detection of the RNA transcription product 90 is indicative of the presence of the suspected polynucleotide of interest 60 in the sample and can be further used for quantitation of the polynucleotide of interest 60. The detection of the transcribed product 90 described above can be accomplished by any means known to one of skill in the art. Preferably, the detection is accomplished using detection of a label incorporated into the transcript 90. Preferably, the detection is performed after or concurrently with size separation of the transcription products.

Ligation

Another means to expedite amplification and/or detection of a small polynucleotide of interest is to include a ligation reaction to further lengthen the small polynucleotide extension product 80. "Ligation" or "covalent coupling" refers to covalent coupling of two adjacent nucleotide sequences, e.g. a linker sequence 100 substantially complementary to, and hybridized to, the spacer segment 30 of the capture probe covalently coupled to an adjacent miRNA or other small polynucleotide extension product 80. The reaction is catalyzed by the enzyme ligase, which forms a phosphodiester bond between the 5'-end of one nucleotide sequence and the 3'-end of the adjacent nucleotide sequence, e.g. between two adjacent segments of the capture probe or complements thereof. Suitable enzymes include the following Ligases: EC 6.5.1.1 (DNA ligase (ATP)) and EC 6.5.1.3 (RNA ligase (ATP)).

Figure 3A:
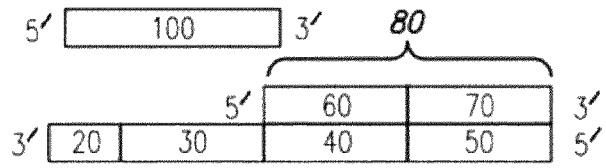
FIG. 3 shows diagrams of some of the steps in certain other embodiments of a method for isolating and detecting miRNAs or other small polynucleotides using a capture probe to guide ligation of a linker according to the present invention.

Following hybridization of the small polynucleotide of interest 60 to the capture probe 10, the method in accordance with this aspect of the present invention further comprises providing a linker segment 100 (FIG. 3A). In one embodiment, the linker segment 100 comprises a substance selected from the group consisting of one or more than one type of polynucleotide, including ribonucleotides and deoxynucleotides, one or more than one type of polynucleotide analog, and a combination of one or more than one type of polynucleotide and polynucleotide analog. In one embodiment, the linker 100 is resistant to nuclease degradation. In a preferred embodiment, the linker 100 comprises nuclease resistant nucleotides. In another preferred embodiment, the linker 100 comprises nucleotides with a phosphothioate backbone that renders the linker resistant to nuclease degradation.

The linker 100 has a linker sequence, and comprises a 3' end and a 5' end. In one embodiment, the linker sequence is substantially complementary to, and capable of hybridizing to, the spacer segment sequence 30 of a capture probe 10 according to the present invention by Watson-Crick base pairing.

The linker 100 comprises between 6 and 50 residues. In a preferred embodiment, the linker 100 comprises at least 10 residues, and at least 10 residues at the 3' end of the linker 100 are exactly the complement of the corresponding residues at or near the 5' end of the spacer segment 30.

Figure 3B:
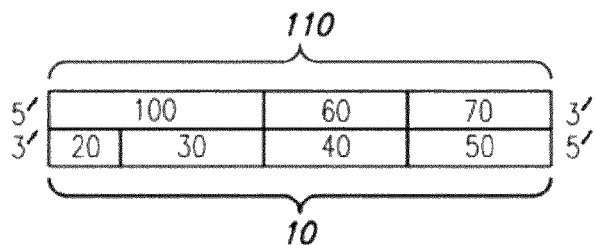

In one embodiment, the linker 100 is allowed to hybridize to the spacer segment 30 and is then ligated to the extension product 80 to form a ligated extension product 110 substantially complementary to, and capable of hybridizing to, the capture probe sequence 10 (FIG. 3B). Such ligation reaction may be assisted by providing a linker 100 having linker sequence specific for the spacer segment sequence 30 of the capture probe 10 so that the small polynucleotide target 60 and said linker 100 are placed in close vicinity to each other upon sequence specific hybridisation.

In a preferred embodiment, the 3' end of the linker 100 is capable of being ligated to the 5' end of a miRNA of interest 60 by a suitable ligase, such as for example T4 polynucleotide ligase, or by another suitable chemical reaction.

Referring now to FIG. 3A, the method then comprises combining the linker 100 with the sample and the capture probe 10, represented in FIG. 3A by the small polynucleotide of interest 60 and the extended segment 70 hybridized to the capture probe 10. In a preferred embodiment, the method comprises combining the linker 100 and the hybridized capture probe/extension product 10/80 in a solution. Alternatively, the capture probe 10, the linker 100 and the sample can be combined simultaneously, or sequentially in any order, as will be understood by those with skill in the art with reference to this disclosure. For example, the capture probe 10 is combined with the sample first, and then the capture probe 10 and sample are combined with the linker 100; or alternately for example, the capture probe 10 and linker 100 are combined first, and then the capture probe 10 and linker 100 are combined with the sample; or alternately for example, the linker 100 is combined with the sample first, and then the capture probe 10 is combined with the linker 100 and the sample.

In one embodiment, combining the capture probe 10, the linker 100 and the sample comprises combining approximately equimolar amounts of the capture probe 10 and the linker 100. In another embodiment, combining the capture probe 10, the linker 100 and the sample comprises combining approximately equimolar amounts of the capture probe 10 and the linker 100 with an amount of sample expected to contain approximately one tenth the molar amount of small polynucleotide of interest 60 as of the capture probe 10 or linker 100. In one embodiment, combining the capture probe 10, the linker 100 and the sample comprises combining the sample with between 0.1 pmoles and 100 pmoles/µl each of the capture probe 10 and the linker 100 in a suitable buffer to create a solution comprising the capture probe 10, the linker 100 and the sample. In a preferred embodiment, the buffer is selected from the group consisting of TRIS, MOPS, and SSC; includes alkali salts such as sodium chloride, lithium chloride, sodium citrate; and may further include nuclease inhibitors and accelerants such as dextran sulfate, polyethylene glycols, polyacrylamides, Exemplary buffers include, (a) 1×TE buffer in 0.1-2.0 M sodium chloride; (b) 0.1M MOPS in 1 mM EDTA and 100 mM sodium chloride, and (c) 20 mM MOPS, 1.8M Lithium Chloride, 1 mM EDTA, 100 µM aurintricarboxylic acid pH 6.8. As will be understood by those with skill in the art with reference to this disclosure, the pH selected for the buffer will be one that optimizes the intended reactions. In general, the pH selected will be between 6 and 8, preferably between 6.4 and 7.4 and more preferably, near 7.0. In a preferred embodiment, the method further comprises adding one or more than one RNAse inhibitor to the combination of the sample and the capture probe 10 such as for example an RNAase or nuclease inhibitor selected from the group consisting of lithium dodecylsulfate (LiDS), sodium dodecylsulfate, the ammonium salt of aurintricarboxylic acid and sodium salt of aurintricarboxylic acid, beta mercaptoethanol, dithiothreitol, Tris(2-Carboxyethyl)-Phosphine Hydrochloride (TCEP) or human placental RNAse inhibitor. Such inhibitors and included to inhibit nucleases without compromising the ability of the probes and their target polynucleotides to hybridize with one another as will be understood by those skilled in the art.

Referring now to FIG. 3B, after combining the linker 100, the capture probe 10 and the sample, the method comprises allowing the linker 100 to hybridize with the spacer segment 30, thereby binding the linker 100, the small polynucleotide of interest 60, and optionally the extended segment 70 to the capture probe 10. In one embodiment, allowing the linker 100 to hybridize with the spacer segment 30 and the small polynucleotide of interest 60 to hybridize with the small polynucleotide binding segment 40 comprises incubating the solution comprising linker 100, the capture probe 10 and the sample for between 1 minute and 60 minutes at between 25° C. and 60° C. under conditions sufficient to hybridize the linker 100 to the spacer segment 30 of the capture probe 10.

In a preferred embodiment, the linker 100 hybridizes to the spacer segment 30 at a position where the last residue on the 3' end of the linker 100 hybridizes to a residue on the spacer segment 30 that is between 1 residue and 5 residues from the 5' end of the small polynucleotide of interest 60. In a particularly preferred embodiment, the linker 100 hybridizes to the spacer segment 30 at a position where the last residue on the 3' end of the linker 100 hybridizes to a residue on the spacer segment 30 that is immediately adjacent to the 5' end of the small polynucleotide of interest 60.

Next, as shown in FIG. 3B, the method comprises covalently ligating the 3' end of the linker 100 that is hybridized to the spacer segment 30 to the 5' end of the small polynucleotide of interest 60 that is hybridized to the small polynucleotide binding segment 40. Ligation of the 3' end of the linker 100 to the 5' end of the small polynucleotide of interest 60, and extension of the 3' end of the small polynucleotide of interest to the 3' end of the extended segment 70 can be accomplished in any order, including simultaneously or sequentially. In one embodiment, the ligation is accomplished by standard techniques, as will be understood by those with skill in the art with reference to this disclosure. In a preferred embodiment, the ligation comprises treating the capture probe 10 with the hybridized linker 100 and the extension product 80 containing a small polynucleotide of interest 60 with a suitable ligase, such as for example T4 polynucleotide ligase in the presence of suitable buffer and essential cofactors for a sufficient time for the ligation to proceed to near total completion of ligation. As will be understood by those with skill in the art with reference to this disclosure, the presence of the spacer segment 30 in the capture probe 10 facilitates the ligation of the linker 100 to the small polynucleotide of interest 60 by aligning the 3' end of the linker 100 with the 5' end of the small polynucleotide of interest 60. The combination of ligation and extension steps produces a "ligated extension product" 110 defined as a strand of linker 100, small polynucleotide of interest 60 and extended segment 70 that have been covalently linked together ("ligated linker-small polynucleotide of interest-extended segment"), and where the ligated extension product 110 is hybridized to the capture probe 10.

In one embodiment, the 5' end of the linker 100 comprises a label, such as for example a fluorescent dye, to facilitate detection, as will be understood by those with skill in the art with reference to this disclosure. Further, the linker 100 can comprise a label, such as for example a fluorescent dye, to facilitate detection at a position other than at the 5' end of the linker 100, as long as the presence of the label does not interfere with other steps of the present method, as will be understood by those with skill in the art with reference to this disclosure. In other embodiments, the linker sequence 100 joined to the small polynucleotide of interest 60 by ligation may accommodate in part primers for PCR amplification or for a labeled detection probe, alone or in combination with the nucleic acid sequence of the adjacent small polynucleotide 60.

Detector Probes

In some embodiments, the detection and identification of the polynucleotide of interest can employ a detector probe. "Detector probe" refers to an a nucleic acid binding molecule capable of recognizing a particular target nucleotide sequence, typically used in an amplification reaction, which can include quantitative or real-time PCR analysis, as well as end-point analysis. Such detector probes can likewise be used to monitor the extension, reverse transcription and/or amplification of the target small polynucleotides, appended segments and/or complements thereof.

Detector probes typically include a fluorescent molecule or fluorophore, including without limitation sulfonate derivatives of fluorescein dyes with $SO_3$ instead of the carboxylate group, phosphoramidite forms of fluorescein, phosphoramidite forms of CY3 or CY5 (commercially available for example from Amersham), aminoallyl, Digoxigenin, Tetramethyl Rhodamine and the like. A wide variety of detectable nucleotide triphospahates are available commercially from Roche (Indianapolis, Ind.), Invitrogen (Carlsbad, Calif.) and others.

The term "Dual-labeled probe" refers to an oligonucleotide with two attached labels. In one aspect, one label is attached to the 5' end of the probe molecule, whereas the other label is attached to the 3' end of the molecule. A particular type of dual-labeled probe contains a fluorescent molecule attached to one end and a molecule which is able to quench this fluorophore by Fluorescence Resonance Energy Transfer (FRET) attached to the other end. Accordingly, a dual-labeled detector probe can also comprise a quencher, including without limitation Black Hole quenchers (Biosearch, Novato, Calif.), Iowa Black (IDT, Coralville, Iowa), QSY quencher (Molecular Probes, Invitrogen, Carlsbad, Calif.), and Dabsyl and Dabcyl sulfonate/carboxylate Quenchers (Epoch, Bothell, Wash.).

"5' nuclease assay probe" refers to a dual-labeled probe which may be hydrolyzed by the 5'-3' exonuclease activity of a DNA polymerase. Probe degradation allows for the separation of the fluorophore and the quencher, resulting in increased fluorescence emission. "5' nuclease assay probes" are often referred to as a "TaqMan assay probes", and the "5' nuclease assay" as "TaqMan assay". These names are used interchangeably in this application.

"Molecular Beacon" refers to a single or dual-labeled probe which is not likely to be affected by the 5'-3' exonuclease activity of a DNA polymerase. Special modifications to the probe, polymerase or assay conditions have been made to avoid separation of the labels or constituent nucleotides by the 5'-3' exonuclease activity of a DNA polymerase. For example, a particular aspect of the molecular beacon may contain a number nuclease resistant residues to inhibit hydrolysis by the 5'-3' exonuclease activity of a DNA polymerase. The detection principle thus relies on a detectable difference in label elicited signal upon binding of the molecular beacon to its target sequence. In one aspect of the invention the oligonucleotide probe forms an intramolecular hairpin structure at the chosen assay temperature mediated by complementary sequences at the 5'- and the 3'-end of the oligonucleotide. The oligonucleotide may have a fluorescent molecule attached to one end and a molecule attached to the other, which is able to quench the fluorophore when brought into close proximity of each other in the hairpin structure.

The detection of binding is either direct by a measurable change in the properties of one or more of the labels following binding to the target (e.g. a molecular beacon type assay with or without stem structure) or indirect by a subsequent reaction following binding, e.g. cleavage by the 5' nuclease activity of the DNA polymerase in 5' nuclease assays. In some embodiments, a dual-labeled probe having an intramolecular hairpin structure, such as the stem-loop and duplex Scorpion™ probes, can serve as both a primer and probe during amplification.

Detector probes can also comprise two probes, wherein for example a fluorophore is on one probe, and a quencher is on the other probe, wherein hybridization of the two probes together on a target quenches the signal, or wherein hybridization on the target alters the signal signature via a change in fluorescence.

In some embodiments, DNA binding dyes, which emit fluorescence when bound to double stranded DNA, can be used to detect double stranded DNA products, which accumulate during amplification. Non-covalently bound minor groove binders (MGB) and/or intercalating labels are used, such as asymmetric cyanine dyes, DAPI, SYBR Green I, SYBR Green II, SYBR Gold, PicoGreen, thiazole orange, Hoechst 33342, Ethidium Bromide, 1-O-(1-pyrenylmethyl) glycerol and Hoechst 33258, thereby allowing visualization in real-time, or end point, of an amplification product in the absence of a detector probe. In some embodiments, real-time visualization can comprise both an intercalating detector probe and a sequence-based detector probe can be employed.

Figure 4A:
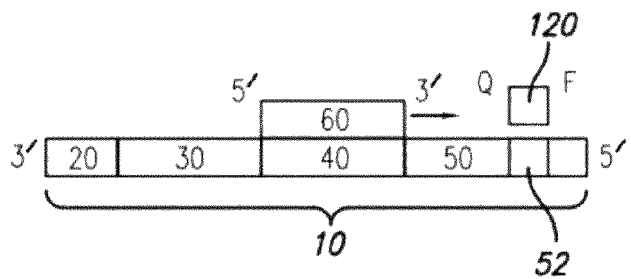
FIG. 4 shows diagrams of some of the steps in other embodiments of a method for detecting miRNAs or other small polynucleotides using a capture probe and a detector probe according to the present invention.

In one embodiment, shown in FIG. 4, the method comprises: (a) providing a sample comprising the small polynucleotide of interest 60, the capture probe 10, and a dual-labeled detector probe 120, having one label attached to the 5' end of detector probe molecule, another label attached to the 3' end of the detector probe 120, and a detector probe sequence that is substantially complementary to, and capable of hybridizing to a detector probe binding sequence 52 within the template segment 50 of the capture probe 10. After combining the sample, capture probe 10 and the detector probe 120, as shown in FIG. 4A, the small polynucleotide of interest 60 is allowed to hybridize with the polynucleotide binding segment 40 and the detector probe 120 is allowed to hybridize with the detector probe binding sequence 52 of the capture probe 10.

Figure 4B:
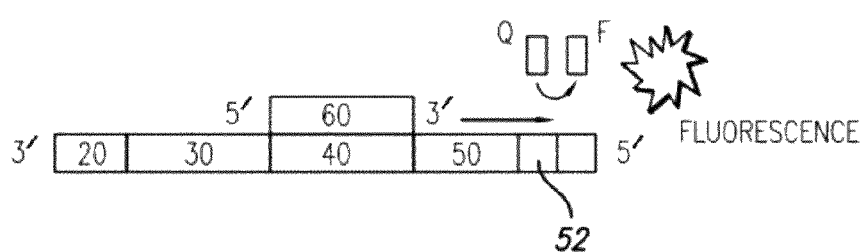

In one embodiment the polynucleotide polymerase preferably has a 5'exonuclease activity capable of cleaving polynucleotides downstream of the hybridized small polynucleotide 60 during extension. As shown in FIG. 4B, upon adding the polymerase and nucleotide mix to the reaction mixture, the hybridized small polynucleotide of interest 60 is extended to form the extension product 80, whereas the detector probe 120 may be hydrolyzed by the 5' to 3' exonuclease of the polynucleotide polymerase. Alternatively, binding of the small polynucleotide of interest 60 is detected by measuring the change in fluorescence properties of one or more of the labels following cleavage of the detector probe 120 and consequent separation of the two labels.

In another embodiment the extended segment 70 of extension product 80 and the detector probe contain complementary sequences recognized by a restriction enzyme. When the detector probe and extended segment are combined to form a double stranded hybridization complex, the detector probe sequence can be recognized and cut by the restriction enzyme. In a preferred embodiment, the restriction enzyme is a nicking endonuclease that "nicks" a single strand of the complex. Alternatively, the extension reaction can include one or more nucleotide analogs in the reaction mixture that render the extended segment resistant to endonuclease action. Nicking of the probe, then provides a detectable change in fluorescence.

Nicked Extension Products

In one embodiment, shown in FIG. 5, the method comprises providing a capture probe 10, where the template segment 50 comprises one or more than one sequence that is one strand of a double stranded restriction enzyme recognition motif 56, referred to herein as a restriction site.

Figure 5A:
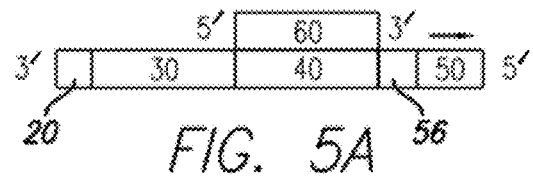
FIG. 5 shows diagrams of some of the steps in other embodiments of a method for isolating and detecting miRNAs or other small polynucleotides using another version of the capture probe that generates a nick site according to the present invention.
Figure 5B:
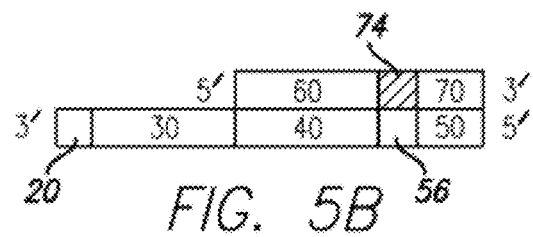

Next, as disclosed above, the method comprises combining the capture probe 10 and the sample, containing the small polynucleotide of interest 60, and allowing the small polynucleotide of interest 60 to hybridize with the small polynucleotide binding segment 40 to form a small polynucleotide/capture probe complex. Next, as shown in FIGS. 5A and 5B, the method comprises an extension reaction, where the small polynucleotide/capture probe complex is combined with a polynucleotide polymerase and a set of nucleotide triphosphates. The extension reaction further comprises extending the hybridized small polynucleotide of interest to form an extension product 80, where the extension product 80 is hybridized to the capture probe 10 to form an extension product/capture probe complex. In one aspect, the extension step converts a single stranded restriction enzyme recognition sequence 56 contained within the template segment 50 of the capture probe 10 into a double stranded restriction enzyme recognition sequence 56 and 74.

In one embodiment the double stranded restriction site 56, 74 can be recognized and acted on by a nicking agent. In a preferred embodiment the restriction site motif 74 of the extended segment 70 can be cut by a nicking endonuclease. In another embodiment, the restriction enzyme recognition motif 56 of the template segment 50 contains one or more than one nucleotide analogue, which protects the template segment 50 from the endonuclease activity of the nicking agent. For example, precise nicking within a restriction site may be facilitated by making certain of its internucleoside bonds resistant to hydrolysis, such as by converting them to phosphorothioate, boranophosphate, methylphosphonate, or peptide bonds, or by substituting a nucleotide variant that is not recognized by a specific restriction endonuclease. In one particular aspect, the specificity of a restriction enzyme may preclude recognition and cutting of a sequence containing dU, substituted for a dT or similarly the use of dI (deoxyinosine) substituted for dG, but still recognize and act upon the complementary sequence of the opposite strand.

Figure 5C:
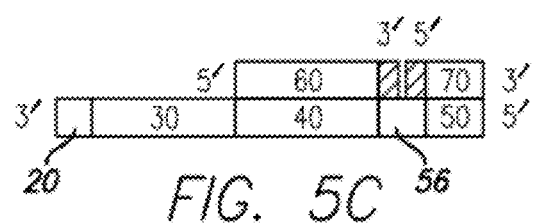

The next step, shown in FIG. 5C, comprises contacting the extension product/capture probe complex with a nicking agent such that the extension product 80 is selectively nicked on one strand of the double stranded restriction site 74 to produce a nicked extension product 82. Nicking of the extension product 80 results in a 3'ended fragment containing the small polynucleotide of interest 60 and a 5'ended fragment containing a portion of the extended segment 70, referred to herein as the nicked extension fragment 82.

Figure 5D:
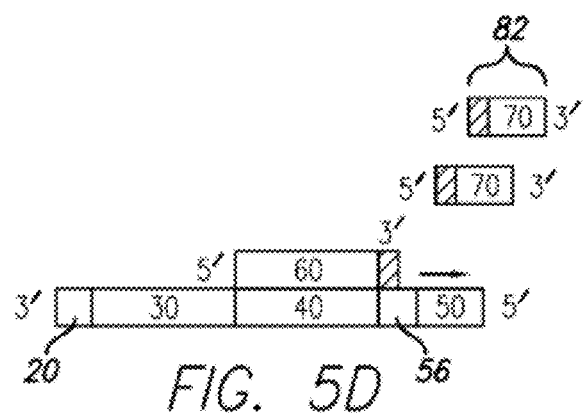

As shown in FIG. 5D, the method further comprises extending the 3'-ended fragment of the nicked extension product containing the hybridized small polynucleotide of interest 60, with a polymerase such that the nicking site is rejuvenated and the nicked extension fragment 82 is displaced.

Displacement of the nicked extension fragment 82 can be facilitated by thermal denaturation and dislodgement of the nicked extension fragment 82. Thus, in preferred embodiments the polymerase and restriction enzymes are thermostable enzymes, which are able to retain enzymatic activity at elevated temperatures suitable for denaturation and dislodgement of the nicked extension fragments. Potentially applicable DNA polymerases include Vent (exo-), Deep Vent (exo-), Pfu (exo-), Bst (large fragment), Bca (exo-), phi 29, (exo-), and Klenow (exo-). Thermophilic polymerases and/or highly processive polymerases, especially those with strand displacement activity, are likely advantageous.

In one embodiment, further cycles of extension, nicking and displacement steps leads to a linear amplification of nicked extension fragments 82, reflecting the initial concentration of the target small polynucleotide 60 originally hybridized to the capture probe 10.

Detecting the Nicked Extension Products

Detection of the nicked extension fragment 82 is indicative of the presence of the suspected polynucleotide of interest 60 in the sample and can be further used for quantitation of the polynucleotide of interest 60. The detection of the nicked extension fragment 82 described above can be accomplished by any means known to one of skill in the art using techniques known in the art including, without limitation, detection of a label incorporated into the nicked extension fragment 82, hybridization and detection of one or more than one nicked extension fragments 82 to a microarray, cloning and sequencing or quantitative Real-Time PCR.

In one embodiment, detection of a nicked extension fragment 82 can be facilitated by contacting an signal generating probe, having a sequence which is complementary to and capable of hybridizing to the displaced nicked extension fragment 82. In a preferred embodiment, the signal generating probe is about 15 to 25 nucleotide residues in length. Hybridization of the signal generating probe to the nicked extension fragment 82 to form a double stranded complex can then be detected using an intercalating dye, such as SYBR green or ethidium bromide, which is capable of producing a fluorescent signal upon selectively binding to double stranded nucleic acids. In a preferred embodiment the nicked extension fragment 82 has a nicked extension fragment sequence that can be correlated with a specific small polynucleotide of interest 60. In a preferred embodiment a first signal generating probe has a first signal generating probe sequence and a second signal generating probe has a second signal generating probe sequence, each having a predetermined sequence or predetermined size, where either the sequence or the size or both the sequence and the size of the first signal generating probe sequence and the second signal generating probe sequence differ from one another. Detecting and distinguishing the sequence and/or size of two or more signal generating probes permits detection of several targets per assay.

In a further embodiment, the signal generating probe can have a fluorophore capable of energy transfer from the intercalating dye. In a preferred embodiment a first signal generating probe has a first fluorophore and a second signal generating probe has a second fluorophore, wherein the fluorescence emission spectrum of the first fluorophore is distinguishable from the fluorescence emission spectrum of the second fluorophore. Detecting and distinguishing the different fluorescence emission spectra of two or more fluorophores permits multiplexing of several targets per assay.

Similarly, in an additional embodiment the signal generating probe which hybridizes with the displaced nicked extension fragment can be a molecular beacon such that in its unhybridized state its quencher and fluor are proximate to one another via its hairpin structure but when hybridized with the displaced nicked extension fragment detectable fluorescence is observed because the fluor and quencher are separated from one another and fluorescence is permitted. Consequently the fluorescence will be proportional to the original small polynucleotide present in the sample. Molecular beacons can be designed to hybridize to unique nicked extension fragments which can be correlated to the targeted small polynucleotide by each uniquely targeted capture probe as discussed above.

In one embodiment, shown in FIG. 6, the method comprises providing a capture probe, where the template segment comprises a first restriction site 56 and a second restriction site 58, where the first restriction site 56 serves as a template to generate a nick site in the extension product 80 or top strand, and the second restriction site 58 is modified to resist nicking of the template segment 50 or bottom strand. Examples of capture probes in accordance with this aspect of the present invention are shown in Table III.

Next, as disclosed above, the method comprises combining the capture probe 10 and the sample, containing the small polynucleotide of interest, and allowing the small polynucleotide of interest 60 to hybridize with the small polynucleotide binding segment 40 to form a small polynucleotide/capture probe complex. Next, the method comprises an extension reaction, where the small polynucleotide/capture probe complex is combined with a polynucleotide polymerase and a set of nucleotide triphosphates. The extension reaction further comprises extending the hybridized small polynucleotide of interest 60 to form an extension product 80, where the extension product 80 is hybridized to the capture probe 10 to form an extension product/capture probe complex. In one aspect, the extension step converts the first restriction site 56 of the capture probe into a double stranded restriction enzyme recognition sequence capable of being nicked on the top strand 74, i.e., the extended segment 70, but not the bottom strand 56, i.e. template segment 50, and conversely the second restriction site 58 in the capture probe is converted into a second double stranded restriction recognition sequence 58, 76, which is not selectively nicked on the corresponding template segment 50

Figure 6A:
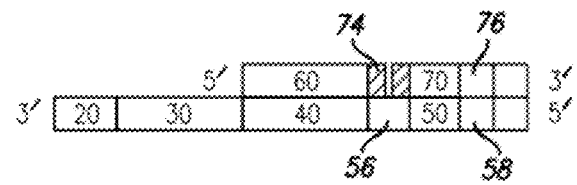
FIG. 6 shows diagrams of some of the steps in other embodiments of a method for detecting miRNAs or other small polynucleotides using another version of the capture probe and a detector probe according to the present invention.

The next step, shown in FIG. 6A, comprises contacting the extension product/capture probe complex with a nicking agent which recognizes and acts on the first restriction site 56, 74, such that the extension product 80 is selectively nicked on one strand, i.e., the top strand 74, of the double stranded restriction site 56, 74 to produce a nicked extension fragment. In one embodiment the nicking agent is a nicking endonuclease and the restriction site motif 74 of the extended segment 70 is cut by the nicking agent. In another embodiment, the restriction enzyme recognition motif of the template segment 50 contains one or more than one nucleotide analogue, which protects the template segment 50 from the endonuclease activity of the nicking agent. For example, precise nicking within a restriction site may be facilitated by making certain of its internucleoside bonds resistant to hydrolysis, such as by converting them to phosphorothioate, boranophosphate, methylphosphonate, or peptide bonds, or by substituting a nucleotide variant that is not recognized by a specific restriction endonuclease. In one particular aspect, the specificity of a restriction enzyme may preclude recognition and cutting of a sequence containing dU, substituted for a dT, but still recognize and act upon the complementary sequence of the opposite strand. Examples of capture probes 10 containing a first Nb.BbvCI or Nt.BbvCI restriction site and a second Nt.AlwI restriction site, where in the second site contains a deoxy-U substituted for deoxy-T are shown in Table III below. Additional examples of capture probes 10 containing a first Nb.BbvCI or Nt.BbvCI restriction site and a second Nt.AlwI restriction site, where in the second site contains a thiolated backbone are also shown in Table III below.

Figure 6B:
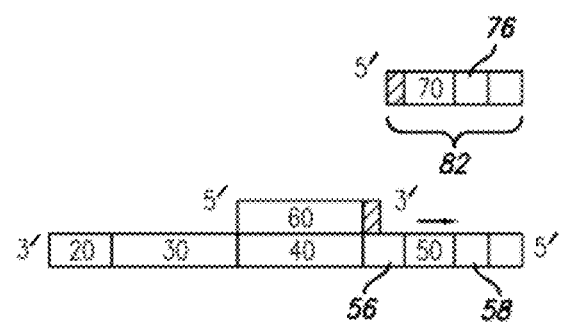
Figure 6C:
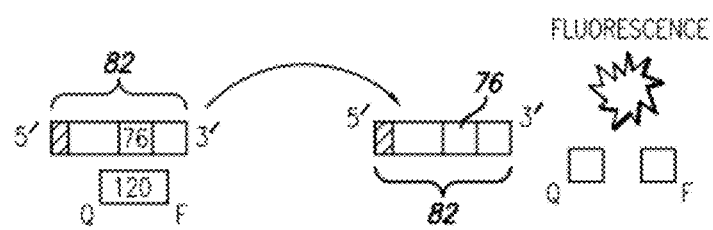

As shown in FIG. 6B, nicking of the extension product 80 results in a 3'ended fragment containing the small polynucleotide of interest 60 and a 5'ended fragment containing a portion of the extended segment 70, referred to herein as the nicked extension fragment 82.

The method further comprises displacement of the nicked extension fragment 82, which contains an unmodified top strand of the second restriction site 76, by the action of the polymerase. In one embodiment, shown in FIG. 6C, detection of a nicked extension segment 82 can be facilitated by contacting a detector probe 120, which is complementary to and capable of hybridizing to the nicked extension fragment 82. Formation of the double stranded probe/nicked extension segment complex regenerates the second double stranded restriction recognition sequence, which is now capable of being nicked on the bottom strand, i.e. the probe sequence 120. In a preferred embodiment, the detection probe is about 15 to 25 nucleotide residues in length.

Next, the method further comprises contacting the double stranded probe/nicked extension segment complex with a nicking agent capable of recognizing and nicking the detection probe sequence 120. In a preferred embodiment the probe is a dual labeled detector probe 120 so that the nicking reaction provides a detectable change in fluorescence. Examples of dual label detector probe sequences in accordance with this particular embodiment are shown in Table IV.

TABLE III

MIRNA CAPTURE PROBES WITH TWO NICK SITES

| PROBE NAME | SEQUENCE 5'-3' | SEQ ID NO: |
|---|---|---|
| 34 AMP dU_HSA[1]- miR-135a | ATCAGGA/ideoxyU[2]/CAGCTGAGCCTCAGCATTC ACATAGGAATAAAAAGCCATAACAC | SEQ ID NO: 24 |

TABLE III-continued

MIRNA CAPTURE PROBES WITH TWO NICK SITES

| PROBE NAME | SEQUENCE 5'-3' | SEQ ID NO: |
|---|---|---|
| 38 AMP dU_HSA[1]-miR-138 | ATCAGGA/ideoxyU[2]/CAGCTGAGCCTCAGCATGA TTCACAACACCAGCTACAC | SEQ ID NO: 25 |
| 56 AMP dU_HSA[1]-miR-154 | ATCAGGA/ideoxyU[2]/CAGCTGAGCCTCAGCATCG AAGGCAACACGGATAACCTAACAC | SEQ ID NO: 26 |
| 34 AMP dU_HSA[1]-miR-135a | ATCAGGATCAG*C*[3]TGAGCCTCAGCATTCACA TAGGAATAAAAAGCCATAACAC | SEQ ID NO: 27 |
| 38 AMP dU_HSA[1]-miR-138 | ATCAGGATCAG*C*[3]TGAGCCTCAGCATGATTCACA ACACCAGCTACAC | SEQ ID NO: 28 |
| 56 AMP dU_HSA[1]-miR-154 | ATCAGGATCAG*C*[3]TGAGCCTCAGCATCGAAGGCA CACGGATAACCTAACAC | SEQ ID NO: 29 |

[1]"HSA" in the names corresponds to the respective Human miRNA bound by a given capture probe
[2]"ideoxyU" corresponds to a dU substitution for T
[3]"*" corresponds to phosphorothioate linkages in the backbone

TABLE IV

DUAL LABEL DETECTION PROBES

| NAME | SEQUENCE 5'-3' | SEQ ID NO: |
|---|---|---|
| QF Probe 1 5'_3' | /5IAbFQ/CAGGATCAGCTGAGAGCC/ IFluorT/CA/3Phos/ | SEQ ID NO: 30 |
| QF Probe 2 5'_3' | /5IAbFQ/CAGGATCAGCTGAGAGCCTCA/ 36-FAM/ | SEQ ID NO: 31 |

"5IAbFQ" corresponds to 5' Iowa Black FQ ™ (IDT)
"IFluorT" corresponds to a fluoroscein labeled T
"36-FAM" corresponds to a 3' terminal fluoroscein Incorporation of DNAzyme Motif In one embodiment, shown in FIG. 7, the method comprises providing a capture probe 10, where the template segment 50 comprises one or more than one sequence that is complementary to a RNA-cleaving catalytic nucleic acid, referred to herein as a "DNAzyme motif" 130. Examples of a RNA-cleaving DNA enzyme (DNAzyme) include the "10-23" and the "8-17" general purpose RNA-cleaving DNA enzymes, which both contain conserved catalytic sequences GGCTAGCTACAACGA (SEQ ID NO:32) and TCCGAGC-CGGACGA (SEQ ID NO:33), respectively. The conserved catalytic domain is flanked by variable binding domains capable of hybridizing to a target RNA by Watson-Crick base pairing. Hybridization of the flanking binding domains to a target RNA results in a loop structure containing the catalytic domain. Cleavage by an exemplary "10-23" DNAzyme occurs at a purine-pyrimidine dinucleotide of the target RNA, whereas cleavage by an exemplary "8-17" DNAzyme can occur at an AG dinucleotide of the target RNA. Accordingly, a DNAzyme complement 130 in accordance with the present embodiment will contain sequences complementary to a conserved catalytic sequence, as will be understood by one of skill in the art with reference to the present disclosure. In addition to a DNAzyme complement motif 130, the template segment 50 in accordance with the present embodiment, comprises a first flanking segment 132 and a second flanking segment 134, flanking the 5'end and the 3'end of the DNAzyme complement, respectively. Preferably, the first flanking segment and second flanking segment are each about five to twenty nucleotide residues in length, more preferably about seven to ten, and most preferably about eight to nine.

In one embodiment, the template segment 50 further comprises a restriction site 56, as described above. In a preferred embodiment, the restriction site 56 is located downstream from, i.e. in the 3' direction, and may overlap with the second probe segment.

Table V provides examples of capture probes containing a DNAzyme complement complementary to the "10-23" conserved catalytic sequences, where the DNAzyme complement is flanked on the 5' end by a nine residues comprising first flanking segment and on the 3'end by nine residues comprising the second flanking segment. In addition the capture probes of Table V all contain a restriction enzyme recognition motif that can be recognized by the nicking endonuclease N.BbvCI (New England Biolabs, Ipswich Mass.).

Next, as disclosed above, the method comprises combining the capture probe and the sample, containing the small polynucleotide of interest 60, and allowing the small polynucleotide of interest 60 to hybridize with the small polynucleotide binding segment 40 to form a small polynucleotide/capture probe complex. Next, the method comprises an extension reaction, where the small polynucleotide/capture probe complex is combined with a polynucleotide polymerase and a set of nucleotide triphosphates. The extension reaction further comprises extending the hybridized small polynucleotide of interest 60 to form an extension product 80, where the extension product 80 is hybridized to the capture probe 10 to form an extension product/capture probe complex.

Figure 7A:
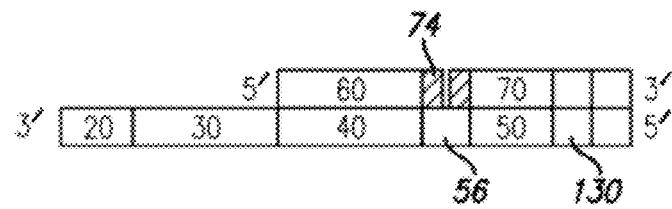
FIG. 7 shows diagrams of some of the steps in other embodiments of a method for isolating and detecting miRNAs or other small polynucleotides using another version of a capture probe capable of generating a DNAzyme according to the present invention.

In a preferred embodiment, shown in FIG. 7A, the next step comprises contacting the extension product/capture probe complex with a nicking agent which recognizes and acts on the restriction site 74, such that the extension product 80 is selectively nicked on one strand, i.e., the top strand 74, of the double stranded restriction site to produce a nicked extension fragment 82.

Figure 7B:
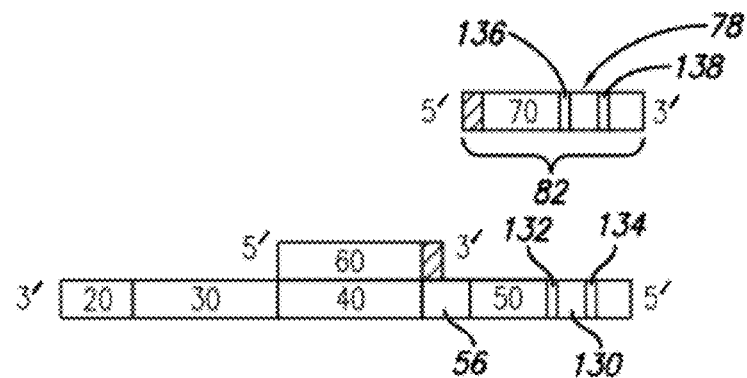
Figure 7C:
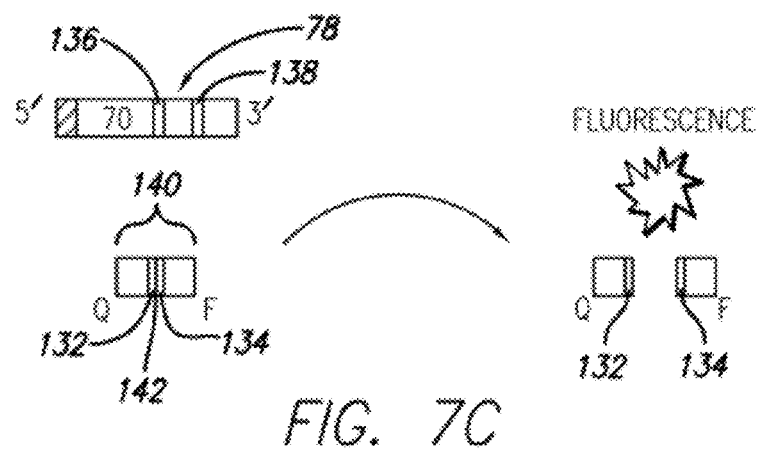

In one embodiment, shown in FIGS. 7B and 7C, displacement of the extension product, or preferably a nicked extension fragment 82, provides a functional DNAzyme capable of hybridizing to and cleaving a suitable substrate. A suitable substrate probe 140 can be an RNA polynucleotide or a chimeric RNA/DNA polynucleotide. The substrate probe 130 comprises a first probe segment 132 having a first probe sequence, a cleavage site and a second probe segment 134 having a second probe sequence. The first probe sequence of the substrate probe 140 is substantially identical to the first flanking sequence 132 of the template segment 50. Likewise, the second probe sequence 134 of the substrate probe 140 is substantially identical to the second flanking sequence 134 of the template segment 50. In a preferred embodiment, the DNAzyme complement motif 78 contains sequence complementary to the "10-23" conserved catalytic domain.

A substrate probe 140 can be a RNA polynucleotide or a chimeric DNA/RNA polynucleotide, having a DNAzyme sensitive cleavage site 142 comprising one or more than one ribonucleotide residue. The substrate probe 140 comprises a first probe segment 132 having a first probe sequence, the cleavage site 142 and a second probe segment 134 having a second probe sequence. The first probe sequence 132 of the substrate probe 140 is substantially identical to the first flanking sequence 132 of the template segment 50. Likewise, the second probe sequence 134 of the substrate probe 140 is substantially identical to the second flanking sequence 134 of the template segment 50. In a preferred embodiment the cleavage site 142 comprises a purine residue adjacent to a pyrimidine residue.

In one embodiment, a loop structure is formed in the nicked extension fragment 82 by Watson-Crick base pairing between the probe sequences 132, 134 and the complementary sequences 136, 138 contained within the extension product 80 or nicked extension fragment 82. Next, the method further comprises nicking the substrate probe at the cleavage site 142. In a preferred embodiment the substrate probe 140 is a dual labeled detector probe so that the nicking step provides a detectable change in fluorescence. Examples of dual labeled substrate probes in accordance with this particular embodiment are shown in Table VI.

TABLE V

CAPTURE PROBES CONTAINING DNAZYME MOTIFS

| NAME | SEQUENCE 5'-3' | SEQ. ID NO. |
|---|---|---|
| S1 DNZ 34hsa-miR-135a | CAGGACGACTCGTTGTAGCTAGCCTGTACCTCA GCATATTCACATAGGAATAAAAAGCCATAAC | SEQ ID NO: 34 |
| S1 DNZ 38hsa-miR-138 | CAGGACGACTCGTTGTAGCTAGCCTGTACCTCA GCATATGATTCACAACACCAGCTAC | SEQ ID NO: 35 |
| S1 DNZ 56hsa-miR-154 | CAGGACGACTCGTTGTAGCTAGCCTGTACCTCA GCATATCGAAGGCAACACGGATAACCTAAC | SEQ ID NO: 36 |
| S2 DNZ 34hsa-miR-135a | ACATTCACCTCGTTGTAGCTAGCCTTGACCTCA GCGAATTCACATAGGAATAAAAAGCCATAAC | SEQ ID NO: 37 |
| S2 DNZ 38hsa-miR-138 | ACATTCACCTCGTTGTAGCTAGCCTTGACCTCA GCGAATGATTCACAACACCAGCTAC | SEQ ID NO: 38 |
| S2 DNZ 56hsa-miR-154 | ACATTCACCTCGTTGTAGCTAGCCTTGACCTCA GCGAATCGAAGGCAACACGGATAACCTAAC | SEQ ID NO: 39 |

TABLE VI

DUAL LABELED DNAZYME SUBSTRATE PROBES

| NAME | SEQUENCE 5'-3' | SEQ ID NO. |
|---|---|---|
| S1 FAM SUBS ZYME1 | /5IABFQ/CAGGACGArCrGrUGTACCTCA/ 36-fam/ | SEQ ID NO: 40 |
| S2 CY3 SUBS ZYME2 | /5IABFQ/ACATTCACrCrGrUTGACCTCA/ 3CY3SP/ | SEQ ID NO: 41 |

Kits

In another embodiment of the present invention, there is provided a kit containing one or reagents for use in the isolation, labeling, and detection of small RNAs, such as for example, human miRNAs. Preferred versions of the kits can include, (a) an equimolar mix of capture probes; (b) a nucleotide mix containing deoxyribonucleotide triphosphates or ribonucleotide triphosphates; (c) a polymerase, (d) streptavidin coated paramagnetic beads; (e) one or more than one dual labeled detector probe, (f) a ligase enzyme; (g) an oligonucleotide linker that is substantially complementary to and capable of hybridizing to the spacer segment of the capture probes; or (h) one or more than restriction enzyme specific for a restriction enzyme recognition sequence contained in the capture probes.

In one embodiment, the kit comprises an equimolar mix of capture extension probes according to the present invention, such as for example those listed in Table II, with the small RNA binding segment comprising complementary sequences to the known human mature miRNA population. In one embodiment, the kit further comprises one or more than one substance selected from the group consisting of labeling buffer comprising 0.5M Tris-HCL, 0.1M $MgCl_2$ 10 mM DTT, 0.5 mg/ml BSA and an RNase inhibitor, such as a recombinant mammalian protein capable of inhibiting eukaryotic RNases; a nucleotide mix containing for example Cyanine 3-dUTP or Cyanine 5-dUTP at 10 micromolar each and unlabeled dATP, dCTP and dGTP at 100 micromolar each; a labeling enzyme such as a polynuclease polymerase for example, Exonuclease-Free Klenow (USB Corp.; Cleveland, Ohio US); capture beads such as 1 micron streptavidin coated paramagnetic beads; bead wash buffer comprising for example 0.5M Tris-HCL, 0.1M $MgCl_2$, and 10 mM DTT; labeled miRNA elution buffer comprising for example formamide; a buffer exchange device such as Microcon® YM 10 devices and 0.1×TE wash buffer.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features.

The foregoing discussion is by no means limiting and other means of detecting the miRNAs labeled and measured by the method of the present invention can readily be envisioned such as the detection of the extended population of miRNAs by electrophoresis, or for example by the extension of the miRNAs where the sample itself serves as the solid phase such as tissue sections. The invention is described in more detail by the following description.

Example 1

One embodiment of the present method was performed as follows. First, a sample of human total RNA from peripheral blood mononuclear cells was labeled using the labeling method as disclosed in this disclosure, and subsequently hybridized to a commercially available miRNA microarray slide, and the fluorescence of the isolated hybridized probes prepared by the method of this disclosure were measured and the results analyzed.

Small RNA Capture-Extension Probe

A set of capture-extension probes comprised miRNA binding segments corresponding to 210 unique human miRNAs and 2 replicates of 3 additional human miRNAs for a total of 216 capture-extension probes were designed to be completely and specifically complimentary to their corresponding human miRNAs, eight (8) examples of which are depicted in Table III with their different miRNA binding segments, with their associated identical solid phase binding segments facilitated by addition of a biotin attached to the 5' end of each capture-extension probe, their identical extension segments, and their identical spacer segments. The small RNA capture-extension probes were obtained from Integrated DNA Technologies, (Coralville, Iowa US). The individual small RNA capture probes were resuspended in 0.1×TE buffer with 2%

Acetonitrile (Sigma Aldrich; St. Louis, Mo. US) at a final concentration of each probe complex of 100 μmol/ul.

TABLE VII

REPRESENTATIVE EXAMPLES OF 5' BIOTINYLATED CAPTURE PROBES AND THEIR COMPLEMENTARY MIRNA

| CAPTURE PROBE NAME | PROBE SEQUENCE | COMPLEMENTARY miRNA | SEQ ID NO: |
|---|---|---|---|
| EPD 1 | /5BIO/ ATTTAGGTGACACTATAGAAACTATACAACC TACTACCTCACCCTATAGTGAGTCGTATTA | hsa-let-7a | SEQ ID NO: 42 |
| EPD 5 | /5BIO/ ATTTAGGTGACACTATAGAACTATACAACCT CCTACCTCACCCTATAGTGAGTCGTATTA | hsa-let-7e | SEQ ID NO: 43 |
| EPD 14 | /5BIO/ ATTTAGGTGACACTATAGAGCTACCTGCACT GTAAGCACTTTTCCCTATAGTGAGTCGTATTA | hsa-miR-106a | SEQ ID NO: 44 |
| EPD 24 | /5BIO/ ATTTAGGTGACACTATAGACGCGTACCAAAA GTAATAATGCCCTATAGTGAGTCGTATTA | hsa-miR-126* | SEQ ID NO: 45 |
| EPD 35 | /5BIO/ ATTTAGGTGACACTATAGATCACATAGGAAT AAAAAGCCATACCCTATAGTGAGTCGTATTA | hsa-miR-135a | SEQ ID NO: 46 |
| EPD 39 | /5BIO/ ATTTAGGTGACACTATAGAGATTCACAACAC CAGCTCCCTATAGTGAGTCGTATTA | hsa-miR-138 | SEQ ID NO: 47 |
| EPD 56 | /5BIO/ ATTTAGGTGACACTATAGACGAAGGCAACA CGGATAACCTACCCTATAGTGAGTCGTATTA | hsa-miR-154 | SEQ ID NO: 48 |
| EPD 201 | /5BIO/ ATTTAGGTGACACTATAGAAATAGGTCAACC GTGTATGATTCCCTATAGTGAGTCGTATTA | hsa-miR-154* | SEQ ID NO: 49 |

"/5BIO/" represents a 5' biotin added in synthesis.

A pool of the 216 capture probes from the Sanger Center was made by adding 7 ul of each probe into one 1.5 ml screw cap tube (Starstedt; Newton, N.C. US). The probes in the mixture were equimolar with respect to one another at a final concentration of approximately 0.5 pmol/each capture probe/ul present in the capture-extension probe mixture.

Hybridization of Small RNA to Pooled Capture Probes

Hybridization was carried out by adding 0.5 ug of total RNA isolated from peripheral blood mononuclear cells (BioChain; Hayward, Calif. US) to 1.0 ul of the pooled capture probes at a concentration of 0.5 pmol/probe/ul and 10 units of RNasin® (Promega; Madison, Wis. US). The components were assembled in Bio-Rad 96-well Multiplate (Bio-Rad Laboratories, Inc.; Hercules, Calif. US) and briefly pulsed in a centrifuge to mix. Hybridization was performed by incubating the components on a thermocycler (Bio-Rad Laboratories, Inc.) at 42° C. for 30 minutes followed by a 1° C. per second decrease to 25° C. for 5 minutes.

Labeling by Extension

Using the capture probe as a template and the hybridized miRNA as a primer, labeling by extension was carried out using Klenow Exonuclease-Free DNA Polymerase (USB; Cleveland, Ohio US). Reaction components containing 1× Klenow Reaction Buffer (USB), 0.1 mM dATP, dGTP, dCPT (Promega Corp.; Madison, Wis. US) with 0.0065 mM Cyanine 3-dUTP (Enzo Life Sciences, Inc.; Farmingdale, N.Y. US) and 5 units Klenow Exonuclease Free DNA Polymerase (USB) were mixed and then added to the wells containing the hybridized miRNA and capture probes for a total of 10 ul reaction volume. The plate was then briefly pulsed in a centrifuge to mix. The plate was covered in foil to protect in from light and incubated at room temperature for one hour. The reaction was stopped by adding 1.0 ul of 0.5M EDTA (Sigma Aldrich Corp.; St. Louis, Mo. US). Electrophoresis to was performed using 1.0 ul of the labeling reaction product run on precast Nuseive/GTG 3:1 agarose gels containing ethidium bromide (BMA CORP.; Rockland, Me. US). The labeling was confirmed by observation of a cluster of bands of the appropriate size for the family of extension products.

Magnetic Bead Capture and Elution Labeled Small RNA from the Capture Probe

The remaining 9 ul of the labeling reaction mix was transferred into a new 1.5 ml screw cap tube (Starstedt; Newton, N.C. US) and 5.0 ul of Streptavidin A-Beads™ (Aureon; Vienna, Austria). The tubes were flicked to mix and incubated to capture the probe-miRNA extension product for 20 minutes at room temperature using foil to protect it from light exposure. After 20 minutes the bead-probe hybrid complex were washed by placing the 1.5 ml tube on a magnet stand (Grace Biolabs; Bend, Oreg. US), and allowing the beads collect at side of tube. The excess liquid was pipetted off and discarded followed by the addition of 100 ul of 1× Klenow Exonuclease Free reaction buffer (USB). The tube was flicked to mix the contents and then placed back onto the magnet stand, excess liquid was drawn off and discarded, and 100 ul of 1× Klenow Exonuclease Free reaction buffer (USB) was added. The tube was mixed, then placed back onto the magnet stand, excess liquid pipetted off and discarded and 20 ul of 100% Deionized Formamide (BioVentures, Inc.; Murfreesboro, Tenn. US) added to the tube to elute the labeled small RNA extension product from the capture probe-bead complex. Two (2) minutes after the formamide was added, the tube was flicked to mix and placed back onto the magnet stand. The 20 ul of formamide containing the eluted labeled small RNA extension product was transferred into a new 1.5 mL screw cap tube. A buffer exchange was then carried out to replace the formamide with 0.1×TE using a Microcon® YM 10 ultrafiltration device (Millipore Corp.; Billerica, Mass. US). 180 ul of 0.1×TE was added to the 20 ul volume containing the eluted labeled small RNA extension product and the entire volume, 200 ul, was transferred to the column placed in a 1.5 ml collection tube. The tube was then spun at 14,000×g in a centrifuge at 10° C. for 30 minutes. The flow through was discarded and the ultrafiltration device placed back into the collection tube and 100 ul of 0.1×TE added to the ultrafiltration device. The ultrafiltration device was then spun again at 14,000×g for 10 minutes at 10° C. and the flow through discarded. The ultrafiltration device was then inverted and placed in a new collection tube and backspun at 3,000×g for 5 minutes at 10° C. The 20 ul of recovered volume contained the labeled small RNA in a suitable buffer for hybridization.

Hybridization of Labeled Small RNA onto Small RNA Biochip 25 ul of 2× Hybridization buffer (Genosensor; Tempe, Ariz. US) was added to the 20 ul of labeled miRNA and 5 ul of sterile DI water, briefly pulsed to mix and pipetted onto the active area of the GenoExplorer™ small RNA BioChip (Genosensor) and covered with a 20×20 plastic coverslip (TedPella, Inc.; Redding, Calif. US). The slide was then placed in a humid chamber, sealed and placed in the dark at room temperature to hybridize overnight for approximately 18 hours. After the overnight incubation, the slide was washed in once in 25 ml of 3×SSC buffer and 0.2% SDS for 5 minutes followed by a second wash in 25 ml of 1×SSC and 0.1% SDS for 5 minutes. A third and fourth wash were done using 0.1×SSC buffer for 2 minutes each. Washing consisted of immersing the slide in the buffer and gentle agitation for the stated amount of time. After washing the slides were air dried with compressed air followed by slide scanning.

Slide Scanning and Analysis

The slide was scanned using a ScanArray® Express HT Microarray Scanner by Perkin Elmer (Wellesley, Mass. US). An easy scan of the full slide at 70% gain and 20 um resolution was sufficient for quantitation by the instrument software. Spot finding and slide information was completed by importing the .gal file provided by the manufacturer of the miRNA microarray. The .gal file included all spot identified as well as location, diameter and spacing of the slide spots.

TABLE VIII

REPRESENTATION OF THE INPUT DATA FOR QUANTITATION

| BEGIN ARRAY PATTERN INFO | |
|---|---|
| Units | μm |
| Array Rows | 4 |
| Array Columns | 1 |
| Spot Rows | 21 |
| Spot Columns | 24 |
| Array Row Spacing | 5000 |
| Array Column Spacing | 5000 |
| Spot Row Spacing | 200 |
| Spot Column Spacing | 200 |
| Spot Diameter | 120 |
| Interstitial | 0 |
| Spots Per Array | 504 |
| Total Spots | 2016 |
| END ARRAY PATTERN INFO | |
| ImageID Channel Image | Fluorophore |
| BEGIN IMAGE INFO | |
| −1 CH1 | Alexa 546 |
| −1 CH2 | Alexa 546 |
| END IMAGE INFO | |
| BEGIN NORMALIZATION INFO | |
| Normalization Method | LOWESS |
| END NORMALIZATION INFO | |

Figure 8:
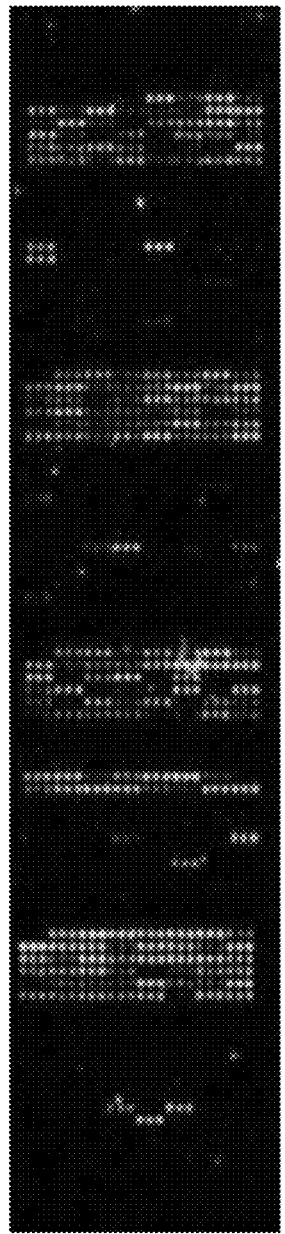
FIG. 8 is a scanned image of the hybridized GenoExplorer™ miRNA chip using 10 um scan resolution and a 70% laser gain.

Referring now to FIG. 8, there is shown a scanned image of the hybridized GenoExplorer™ miRNA chip using 10 um scan resolution and a 70% laser gain.

According to the miRNA microarray slide layout, each spot in printed in triplicate allowing for spot to spot normalization within each spot, as well as across the entire slide. In addition to miRNA spots, there were negative control spots consisting of either buffer only or other unknown sequences that should not fluoresce with the addition of sample. The GenoExplorer™ miRNA chip contains a total of 632 spots representing mature and precursor miRNAs in triplicate. The mean and median intensities of all the negative control spots were averaged to give a representative value for background levels. Each mean and median intensity value of the background was subtracted from the mean and median intensity value of the sample spots to give a signal minus noise value. Once obtained, the individual sample values were averaged across there triplicate values to give an average signal intensity value for each represented sample spot. Those sample spots with high standard deviations between the triplicate spots were not used for final analysis as they did not accurately represent the sample intensity. Overall 198 of the 216 capture probes that were added to the total RNA sample for small RNA extension labeling were considered positive once normalized. The log base 2 ($log_2$) or signal intensities after normalization and ranged from a positive low of 4.64 to a positive high of 13.28. The miRNA, hsa-mir-198, corresponded to the highest signal intensity of $log_2$ 13.28 with a spot to spot standard deviation of $log_2$ 0.099. Additional spots were present but thrown out due to one of the triplicate spots lying outside an acceptable intensity range compared to the other triplicate spots.

Figure 9:
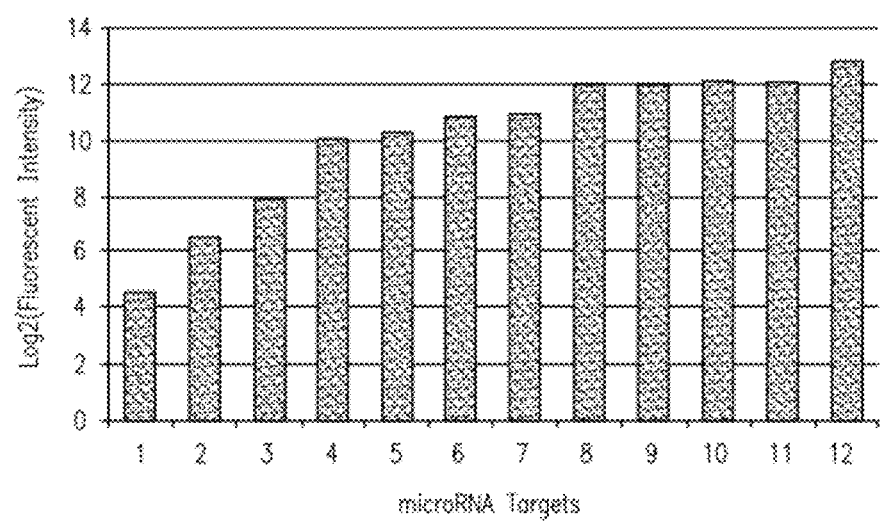
FIG. 9 is a graph of fluorescent intensity for the sample of 12 different miRNAs detected using a method according to the present invention.

Referring now to FIG. 9, there is shown a graph of fluorescent intensity for the sample of 12 different miRNAs detected in 0.5 ug of human total RNA isolated from peripheral blood mononuclear cells using cyanine 3, where the 12 different miRNAs detected were from 1 to 12: 135a, 369, 024, 453, 154, 7e, 154*, 138, 325, 106a, 126 and 7a.

The specific of miRNAs represented in peripheral blood mononuclear cells was unknown before conducting this experiment. Most miRNA microarray studies are performed on specific tissue such as tumor and non tumor. The results of this microarray show that using the method of the present invention the capture-extension probes can specifically capture and facilitate labeling the miRNAs present in a total RNA sample and the labeled product is useful for downstream applications such as microarray analysis. In this example a relatively small sample size of 0.5 ug of total RNA was used and resulted in acceptable signal intensities when hybridized onto a microarray. Most current labeling methods require as much as 50 ug of starting total RNA material in order to receive acceptable signal intensity levels after slidehybridization.

Example 2

To illustrate the nick-amplification method the following experiment was performed. In brief, synthetic microRNAs were amplified, detected and analyzed using the method and reagents described below.

Small RNA Nick-Amplification Probes

A small set of nick-amplification probes was designed to be completely and specifically complementary to a set of human microRNAs (miRNAs). The set of nick-amplification probes was obtained from Integrated DNA Technologies, (Coralville, Iowa US). Each of the individual probes was resuspended in 0.1×TrisEDTA (Sigma Aldrich: St. Louis, Mo. US) with 2% acetonitrile (Sigma Aldrich) at a final concentration of 100 pmol/μl.

| NICK-AMP PROBE NAME | PROBE SEQUENCE 5'-3' | COMPLE-MENTARY miRNA | SEQ ID NO: |
|---|---|---|---|
| 34 AMP dU_hsa-miR-135a | ATCAGGA/ideoxyU/CAGCTGA GCCTCAGCATTCACATAGGAA TAAAAAGCCATAACAC | hsa-miR-135a | SEQ ID NO: 24 |
| 38 AMP dU_hsa-miR-138 | ATCAGGA/ideoxyU/CAGCTGA GCCTCAGCATGATTCACAACA CCAGCTACAC | hsa-miR-138 | SEQ ID NO: 25 |
| 56 AMP dU_hsa-miR-154 | ATCAGGA/ideoxyU/CAGCTGA GCCTCAGCATCGAAGGCAAC ACGGATAACCTAACAC | hsa-miR-154 | SEQ ID NO: 26 |

Synthetic microRNAs

The synthetic miRNA (syn-miRNA) were selected and designed to specifically reflect a set of human miRNAs. The syn-miRNAs were obtained from Integrated DNA Technologies (Coralville, Iowa US). The syn-miRNA were resuspended in stabilization buffer containing 1 mM Sodium Citrate (Ambion; Austin, Tex. US) and 30% Formamide (Bioventures; Murfreesboro, Tenn. US) at a final concentration of 100 pmol/ul. The syn-miRNAs were then aliquoted into 10 μl working stocks in 0.5 ml tubes (Nalgene; Rochester, N.Y.) to reduce freeze-thaw effects.

| SYNTHETIC MICRORNA NAME | RNA SEQUENCE 5'-3' (rN = ribonucleotide) | HUMAN miRNA | SEQ ID NO: |
|---|---|---|---|
| hsa-miR-138 | /5Phos/rArGrCrUrGrGrUrGrUrUrGrUrGrArArUrC | hsa-miR-138 | SEQ ID NO: 50 |
| hsa-miR-135a | /5Phos/rUrArUrGrGrCrUrUrUrUrUrArUrUrCrCrUrArUrGrUrGrA | hsa-miR-135a | SEQ ID NO: 51 |
| hsa-miR-154 | /5Phos/rUrArGrGrUrUrArUrCrCrGrUrGrUrUrGrCrCrUrUrCrG | hsa-miR-154 | SEQ ID NO: 52 |

Quencher/Fluor Probes

A quencher/fluor (QF) probe was designed to be recognized and nicked by nicking enzyme Nb.BbvC1A. The 5IAbFQ refers to a 5' Iowa Black fluorescent quencher that will quench the FAM fluorescence until the probe is nicked or cut by one or more suitable enzyme. The QF probe was obtained from Integrated DNA Technologies, (Coralville, Iowa). The probe was resuspended in 0.1×TE with 2% acetonitrile (Sigma Aldrich: St. Louis, Mo.) at a final concentration of 100 pmol/µl.

| Q-F PROBE NAME | PROBE SEQUENCE 5'-3' | NICKING ENZYME SITE | SEQ ID NO: |
|---|---|---|---|
| QF PROBE 2 | 5'/5IAbFQ/CAGGATCAGCTGAGAGC CTCA/36-FAM/3' | Nb.BbvCI | SEQ ID NO: 31 |

Nick Extension and Amplification Reaction

All reaction components were thawed and assembled on ice to minimize any enzyme activity before the desired reaction start time and or temperature. Six (6) different reactions with four (4) duplicates of each reaction were assembled using the following master mix: 1×NEB Buffer 2 (New England Biolabs; Ipswich, Mass. US), 50 µM dNTP mix (each dA, dC, dG, dT, (Bioventures, Inc.)), 0.05 pmol of syn-miRNA, 1 pmol of Nick-Amp Probe, 1 pmol of QF Probe, 2 units of Exonuclease-Free Klenow (USB Corporation; Cleveland, Ohio US), 1 unit of Nt.AlwI enzyme (New England Biolabs), 1 unit of Nb.BbvCI (New England Biolabs) and sterile nuclease-free water to a final volume of 20 µl per reaction. The 6 reactions differed in their syn-miRNA and Nick-Amp probe combination according to the following matrix; all reactions contained the same QF probe:

| | syn-miRNA Name | Nick-Amp Probe Name |
|---|---|---|
| REACTION 1 | hsa-miR-135a | 34 AMP dU_hsa-miR-135a |
| REACTION 2 | None | 34 AMP dU_hsa-miR-135a |

-continued

| | syn-miRNA Name | Nick-Amp Probe Name |
|---|---|---|
| REACTION 3 | hsa-miR-138 | 38 AMP dU_hsa-miR-138 |
| REACTION 4 | None | 38 AMP dU_hsa-miR-138 |
| REACTION 5 | hsa-miR-154 | 56 AMP dU_hsa-miR-154 |
| REACTION 6 | None | 56 AMP dU_hsa-miR-154 |

Once all reactions were assembled on ice, 20 µl was then pipetted into the wells of pre-chilled 0.2 ml low profile white strip tubes (Bio-Rad; Hercules, Calif. US) strips. The strips were then capped with 0.2 ml clear flat cap strips from Bio-Rad and placed on a Chromo4 Real Time PCR instrument (BioRad). The reactions were performed using the following program programmed using Opticon Monitor2 software (Bio-Rad): Step 1: 5 minute hold at 4° C., plate read, Step 2: 37° C. for 30 seconds, plate read, Step 3: go to Step 2 99 more times, Step 4: plate read, End. Upon completion of the program the data was analyzed as follows.

Nick Amplification Analysis

Opticon Monitor2 software was used to analyze the results of the Nick-Amplification reactions. A manual threshold of 0.04 fluorescence, was set to allow for any initial fluorescence that was present before the reactions started. The results show that for all reactions with synthetic microRNAs present in the reaction, the fluorescence signal increased above background at 2 to 3.9 times the C(t) of the no microRNA reactions. The chart below gives the average cycle count, C(t), across the 4 replicates for each reaction, at which each reaction signal crossed above the set threshold value (0.04 Fluorescence).

| WELL RANGE | REACTION NAME | SYN-MIRNA | NICK-AMP PROBE | C(t) AVERAGE |
|---|---|---|---|---|
| C1-F1 | Reaction 1 | hsa-miR-135a | 34 AMP dU_hsa-miR-135a | 39.95 |
| C3-F3 | Reaction 2 | None | 34 AMP dU_hsa-miR-135a | 79.91 |
| C5-F5 | Reaction 3 | hsa-miR-138 | 38 AMP dU_hsa-miR-138 | 17.58 |
| C7-F7 | Reaction 4 | None | 38 AMP dU_hsa-miR-138 | 50.87 |
| C9-F9 | Reaction 5 | hsa-miR-154 | 56 AMP dU_hsa-miR-154 | 24.98 |
| C11-F11 | Reaction 6 | None | 56 AMP dU_hsa-miR-154 | 99.08 |

The present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A method of detecting a small polynucleotide of interest, comprising:
    (a) providing one or more than one capture probe, the capture probe comprising a polynucleotide, the polynucleotide comprising:
        a template segment comprising a template segment sequence, the template segment comprising a 3' end and a 5' end, the template segment sequence comprising one or more than one sequence that is one strand of a double stranded restriction enzyme recognition sequence; and
        a small polynucleotide binding segment comprising a small polynucleotide binding segment sequence, the small polynucleotide binding segment comprising a 3' end and a 5' end, wherein the small polynucleotide binding sequence is substantially complementary to, and capable of hybridizing to, one or more than one small polynucleotide of interest by Watson-Crick base pairing;
        wherein the 3' end of template segment is connected to the 5' end of the small polynucleotide binding segment;
        wherein the restriction enzyme recognition sequence is not present in the small polynucleotide of interest and the small polynucleotide binding segment;
    (b) providing a sample comprising a small polynucleotide of interest, wherein the small polynucleotide of interest is selected from the group consisting of a RNA polynucleotide, a DNA polynucleotide and a combination thereof;
    (c) combining the capture probe and the sample;
    (d) allowing the small polynucleotide of interest to hybridize with the small polynucleotide binding segment of the capture probe to form a small polynucleotide/capture probe complex;
    (e) combining the small polynucleotide/capture probe complex with a polynucleotide polymerase and a set of nucleotide triphosphates; and
    (f) extending the hybridized small polynucleotide of interest to form an extension product, the extension product comprising the small polynucleotide of interest connected at the 3' end to an extended segment, the extended segment comprising an extended segment sequence, the extended segment sequence comprising a sequence complementary to the template segment of the capture probe, wherein the extension product is hybridized to the capture probe to form an extension product/capture probe complex, the extended segment sequence and the template segment sequence comprising a double stranded restriction enzyme recognition sequence;

(g) providing a restriction enzyme that recognizes and acts upon the restriction enzyme recognition sequence of the extended segment;

(h) contacting the restriction enzyme with the restriction enzyme recognition sequence;

(i) nicking the extension product at or near the restriction enzyme recognition sequence of the extended segment, but not the template segment, to produce a 3' ended fragment containing the small polynucleotide of interest and a 5' ended nicked extension fragment; and (j) extending the 3'-ended fragment containing the hybridized small polynucleotide of interest with a polymerase such that the restriction enzyme recognition sequence is rejuvenated and the 5'-ended nicked extension fragment is displaced; and (k) detecting the nicked extension fragment.

2. The method of claim 1, wherein the restriction enzyme recognition sequence is recognized by a nicking endonuclease.

3. The method of claim 1, wherein the restriction enzyme recognition sequence of the template segment contains one or more than one nucleotide analogue, which renders the restriction enzyme recognition sequence of the template segment resistant to the endonuclease activity of the restriction enzyme.

4. The method of claim 1, wherein:
(a) the template segment of the capture probe comprises a first restriction site and a second restriction site, wherein the first restriction site differs from the second restriction site and the second restriction site is modified to resist nicking of the template segment;
(b) the extension step converts the first restriction site into a first double stranded restriction enzyme recognition sequence capable of being nicked on the extended segment, but not the template segment, and the second restriction site is converted into a second double stranded restriction recognition sequence;
(c) the nicking step comprises contacting the extension product/capture probe complex with a first nicking agent which recognizes and acts on the first restriction site, such that the extension product is selectively nicked at or near the first restriction site of the extended segment to produce a nicked extension fragment; and
(d) the detecting step comprises:
(1) providing a dual labeled detector probe, which is complementary to and capable of hybridizing to the nicked extension fragment;
(2) hybridizing the probe to the nicked extension fragment to form a double stranded probe/nicked extension fragment complex;
(3) contacting the double stranded probe/nicked extension fragment complex with a second nicking agent capable of recognizing the second double stranded restriction recognition sequence and nicking the detector probe sequence; and
(4) detecting a change in fluorescence associated with nicking the dual labeled detector probe.

5. The method of claim 4, wherein the first double stranded restriction enzyme recognition sequence is recognized by a nicking endonuclease.

6. The method of claim 4, wherein the second restriction site of the template segment contains one or more than one nucleotide analogue, which renders the template segment resistant to the endonuclease activity of the restriction enzyme.

7. The method of claim 1, wherein:
(a) the template segment further comprises one or more than one DNAzyme complementary sequence that is complementary to a DNAzyme motif, a first flanking segment and a second flanking segment, the first flanking segment flanking the 5' end of the DNAzyme complementary sequence and the second flanking segment flanking the 3' end of the DNAzyme complementary sequence;
(b) the displacement of the nicked extension fragment provides a functional DNAzyme capable of hybridizing to and cleaving a suitable substrate probe at a DNAzyme cleavage site;
(c) the detecting step further comprising;
(1) providing suitable substrate probe comprising an RNA polynucleotide or a chimeric RNA/DNA polynucleotide, the substrate probe having one label attached to the 5' end of the substrate probe molecule and another label attached to the 3' end of the substrate probe, the substrate probe comprising a first substrate probe segment having a first substrate probe sequence, a DNAzyme cleavage site and a second substrate probe segment having a second substrate probe sequence, wherein first substrate probe sequence of the substrate probe is substantially identical to the first flanking segment of the template segment and the second substrate probe sequence is substantially identical to the second flanking sequence of the template segment;
(2) contacting the substrate probe and the nicked extension fragment such that a loop structure containing the DNAzyme motif is formed in the nicked extension fragment by Watson-Crick base pairing between the first substrate probe sequence and complementary sequences contained within the nicked extension fragment and between the second substrate probe and complementary sequences contained within the nicked extension fragment;
(3) cleaving the substrate probe at the DNAzyme cleavage site; and
(4) detecting a change in fluorescence associated with cleaving the substrate probe.

8. The method of claim 7, the one or more than one capture probe comprising a composition containing two or more capture probes, the composition comprising:
(a) a first capture probe having a first spacer segment, a first small polynucleotide binding segment and a first template segment; and
(b) a second capture probe having a second spacer segment, a second small polynucleotide binding segment and a second template segment, wherein the second small polynucleotide binding segment comprises a different polynucleotide binding segment sequence than the first polynucleotide binding segment and the second template segment comprises a different template segment sequence than the first template segment.

9. The method of claim 1, wherein the small polynucleotide of interest is selected from the group consisting of miRNAs, snoRNAs, siRNAs and short interfering RNAs.

10. The method of claim 1, wherein the capture probe further comprises a solid phase binding segment and the small polynucleotide/capture probe complex or the extension product/capture probe complex is captured to a solid phase by binding of capture probe to a solid support via the solid phase binding segment.

11. The method of claim 1, wherein one or more than one of the nucleotide triphosphates contains a detectable label and the extended segment contains one or more than one labeled nucleotide residue.

12. The method of claim 1, further comprising amplifying the nicked extension product and the capture probe by a polymerase chain reaction.

13. The method of claim 3, the one or more than one nucleotide analogue comprising a deoxyuridine substituted for a deoxythymidine in a restriction enzyme recognition sequence.

14. The method of claim 3, the one or more than one nucleotide analogue comprising a deoxyinosine substituted for a deoxyguanosine in a restriction enzyme recognition sequence.

15. The method of claim 3, the restriction enzyme recognition sequence than comprising one or more than one internucleoside bond resistant to hydrolysis.

16. The method of claim 15, wherein the one or more than one internucleoside bond is selected from the group consisting of phosphorothioate, boranophosphate, methylphosphonate and peptide bonds.

17. The method of claim 4, the second restriction site comprising one or more than one nucleotide analogue.

18. The method of claim 17, the one or more than one nucleotide analogue comprising a deoxyuridine substituted for a deoxythymidine in the second restriction enzyme recognition sequence.

19. The method of claim 17, the one or more than one nucleotide analogue comprising a deoxyinosine substituted for a deoxyguanosine in a restriction enzyme recognition sequence.

20. The method of claim 17, the restriction enzyme recognition sequence comprising one or more that one internucleoside bond resistant to hydrolysis.

21. The method of claim 20, wherein the one or more than one internucleoside bond is selected from the group consisting of phosphorothioate, boranophosphate, methylphosphonate and peptide bonds.

22. The method of claim 2, wherein the nicking endonuclease is selected from the group consisting of N.BbvCI, N.AlwI, N.BstNBI and N.Bpu10I.

23. The method of claim 5, wherein the nicking endonuclease is selected from the group consisting of N.BbvCI, N.AlwI, N.BstNBI and N.Bpu10I.

24. The method of claim 6 wherein the second double stranded restriction enzyme recognition sequence is recognized by a nicking endonuclease.

25. The method of claim 24, wherein the nicking endonuclease is selected from the group consisting of N.BbvCI, N.AlwI, N.BstNBI and N.Bpu10I.

* * * * *

UNITED STATES PATENT AND TRADEMARK OFFICE
CERTIFICATE OF CORRECTION

| | | |
|---|---|---|
| PATENT NO. | : 8,329,394 B2 | Page 1 of 1 |
| APPLICATION NO. | : 11/958180 | |
| DATED | : December 11, 2012 | |
| INVENTOR(S) | : Dawson et al. | |

It is certified that error appears in the above-identified patent and that said Letters Patent is hereby corrected as shown below:

In claim 15, col. 61, line 23: after "sequence" delete the word "than"

Signed and Sealed this
Twenty-second Day of January, 2013

David J. Kappos
*Director of the United States Patent and Trademark Office*